US006197059B1

(12) United States Patent
Cumming

(10) Patent No.: US 6,197,059 B1
(45) Date of Patent: *Mar. 6, 2001

(54) ACCOMODATING INTRAOCULAR LENS

(75) Inventor: J. Stuart Cumming, Anaheim, CA (US)

(73) Assignee: Medevec Licensing, B.V. (NL)

(*) Notice: Subject to any disclaimer, the term of this patent is extended or adjusted under 35 U.S.C. 154(b) by 0 days.

This patent is subject to a terminal disclaimer.

(21) Appl. No.: 08/987,531

(22) Filed: Dec. 9, 1997

Related U.S. Application Data

(63) Continuation-in-part of application No. 08/640,118, filed on Apr. 30, 1996, now abandoned, which is a continuation of application No. 08/500,010, filed on Jul. 10, 1995, now abandoned, which is a continuation of application No. 08/113,215, filed on Aug. 27, 1993, now abandoned, which is a continuation-in-part of application No. 08/020,630, filed on Feb. 22, 1993, now Pat. No. 5,476,514, which is a continuation-in-part of application No. 07/915,453, filed on Jul. 16, 1992, now abandoned, which is a continuation-in-part of application No. 07/515,636, filed on Apr. 27, 1990, now abandoned.

(51) Int. Cl.[7] .................................................. A61F 2/16
(52) U.S. Cl. ...................... 623/6.39; 623/6.43; 623/6.47
(58) Field of Search ................................ 623/4, 6, 6.39, 623/6.43, 6.46, 6.47, 6.49; 606/4, 5

(56) References Cited

U.S. PATENT DOCUMENTS

| 4,254,509 | * | 3/1981  | Tennant ............................... 623/6 |
| 4,424,597 | * | 1/1984  | Schlegel ............................... 623/6 |
| 4,585,457 | * | 4/1986  | Kalb .................................... 623/6 |
| 4,673,406 | * | 6/1987  | Schlegel ............................... 623/6 |
| 4,704,123 | * | 11/1987 | Smith .................................. 623/6 |
| 4,759,761 | * | 7/1988  | Portnoy ............................... 623/6 |
| 4,936,850 | * | 6/1990  | Barrett ................................ 623/6 |
| 5,047,051 | * | 9/1991  | Cumming ............................ 623/6 |
| 5,171,319 | * | 12/1992 | Keates et al. ....................... 623/6 |
| 5,217,490 | * | 6/1993  | Sayano et al. ..................... 623/6 |

* cited by examiner

Primary Examiner—Jeffrey A. Smith
Assistant Examiner—Eduardo C. Robert
(74) Attorney, Agent, or Firm—Boniard I. Brown

(57) ABSTRACT

An accommodating intraocular lens to be implanted within the natural capsular bag of a human eye from which the natural lens matrix has been removed through an anterior capsule opening in the bag circumferentially surrounded by an anterior capsular remnant. During a postoperative healing period following surgery, the anterior capsular remnant fuses to the posterior capsule of the bag by fibrosis about haptics on the implanted lens while the ciliary muscle is maintained in its relaxed state by a cycloplegic to prevent dislocation of the lens, and the lens is deflected rearwardly by the fibrosing anterior capsular remnant to a distant vision position against the elastic posterior capsule of the bag in which the posterior capsule is stretched rearwardly. After fibrosis is complete, natural brain-induced contraction and relaxation of the ciliary muscle relaxes and stretches the fibrosed anterior remnant and increases and reduces vitreous pressure in the eye to effect vision accommodation by the remnant, the posterior capsule, and vitreous pressure. A method of utilizing the intraocular lens to provide a patient with vision accommodation.

25 Claims, 19 Drawing Sheets

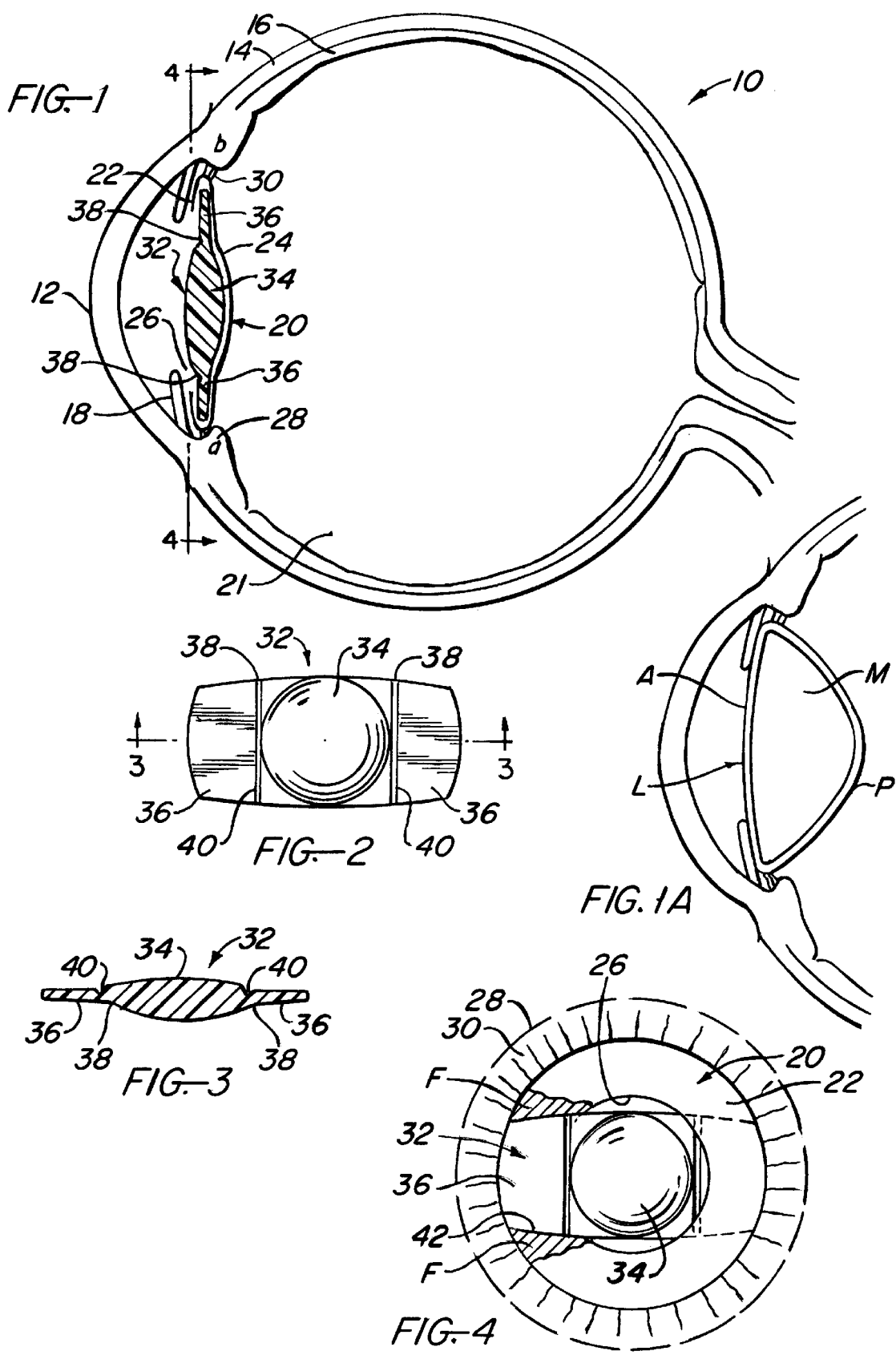

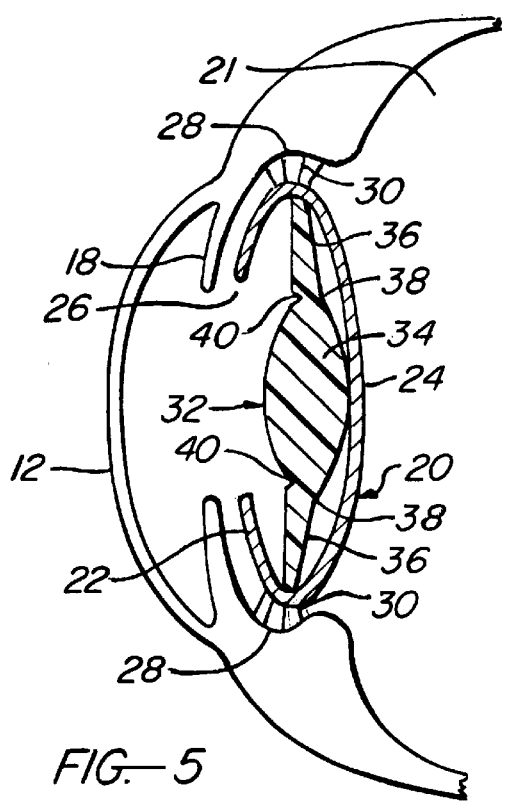
FIG.—5
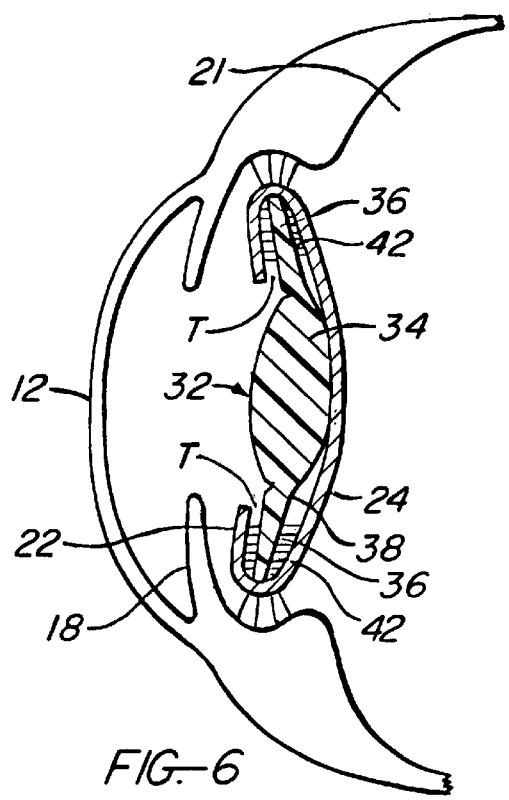
FIG.—6
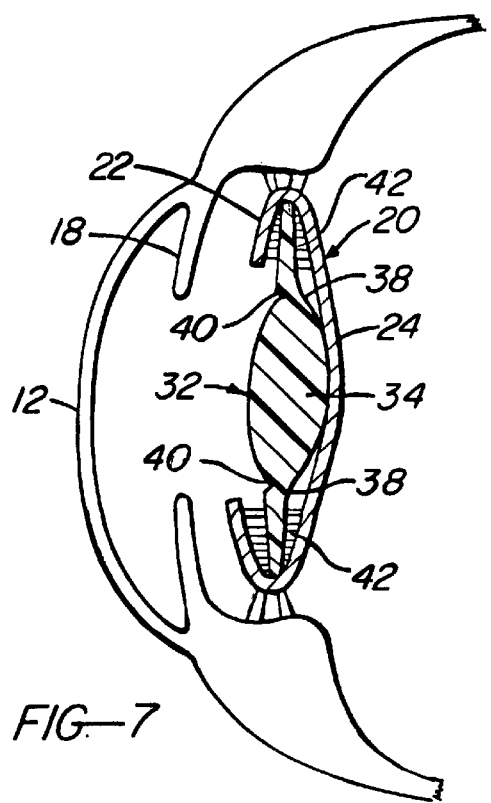
FIG.—7
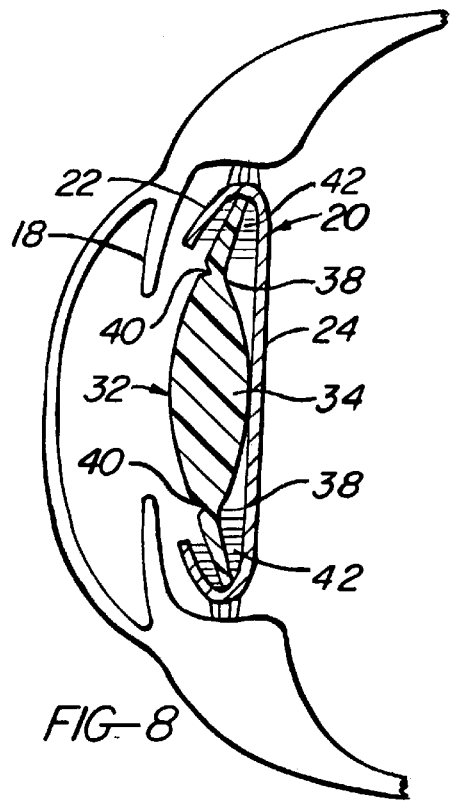
FIG.—8

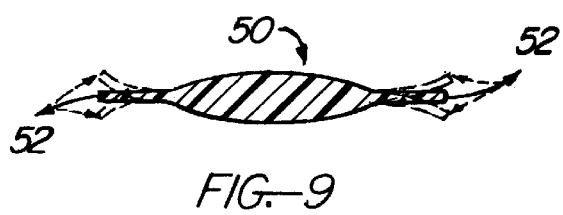
FIG.-9
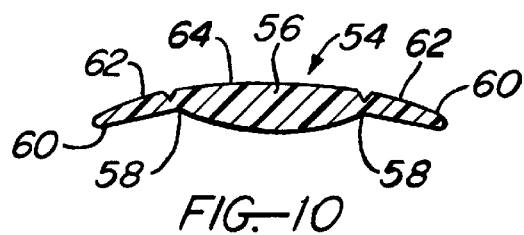
FIG.-10
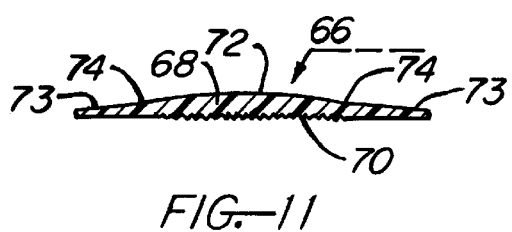
FIG.-11
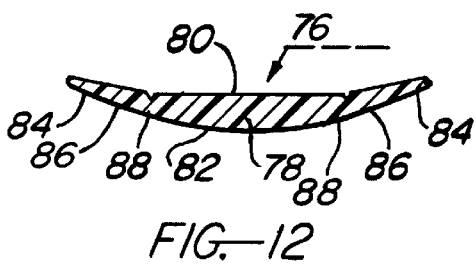
FIG.-12
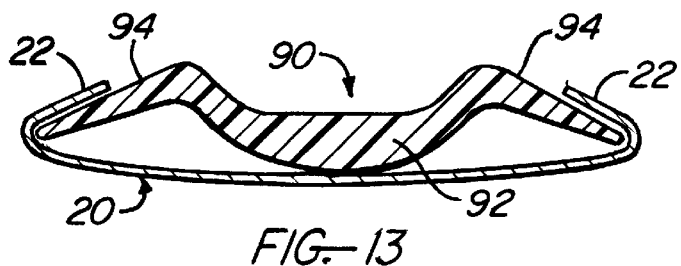
FIG.-13
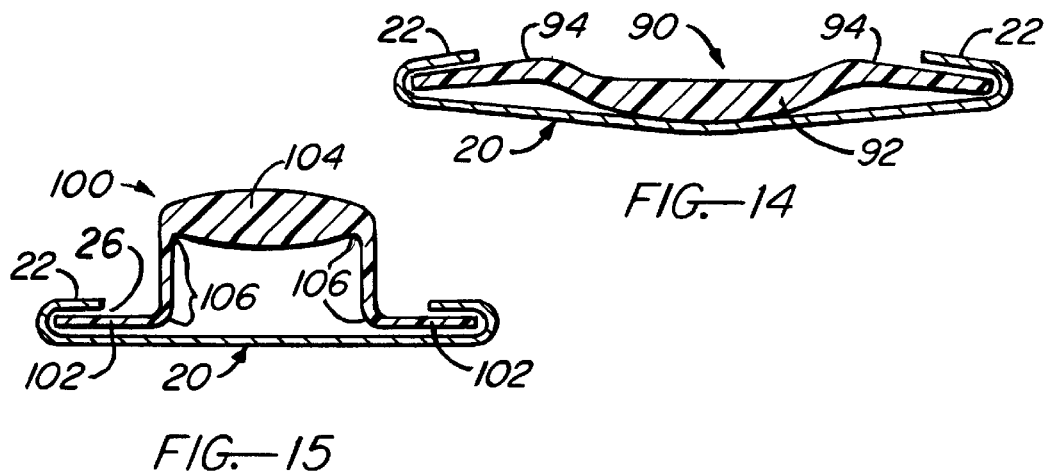
FIG.-14
FIG.-15

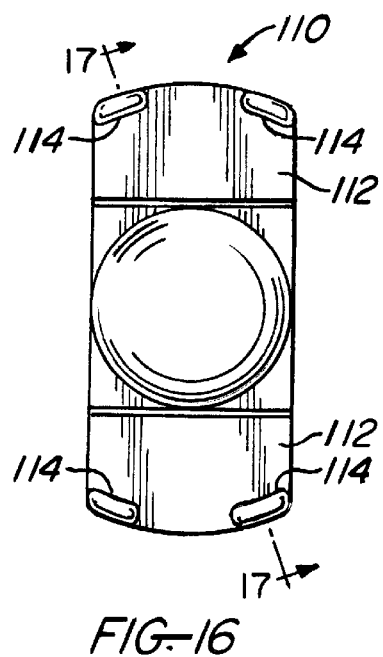
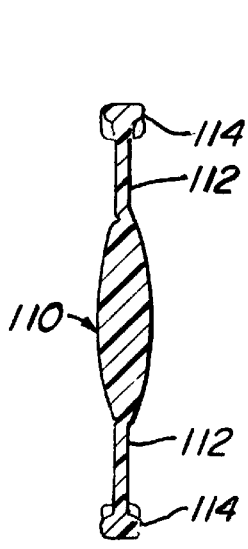
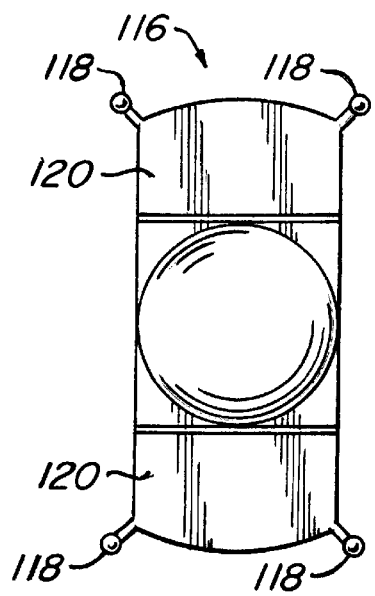
FIG.-16          FIG.-17          FIG.-18
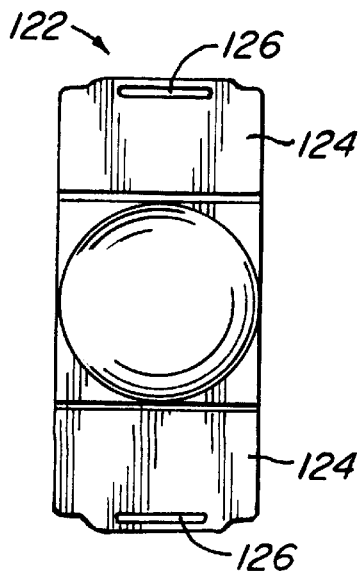
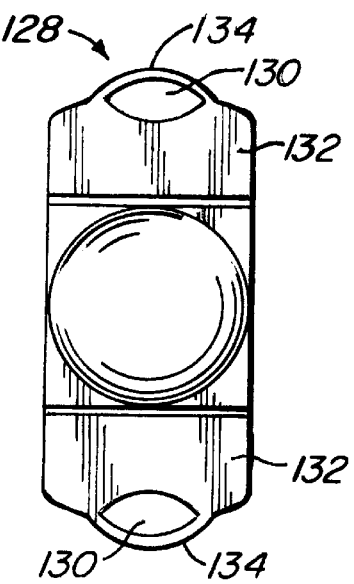
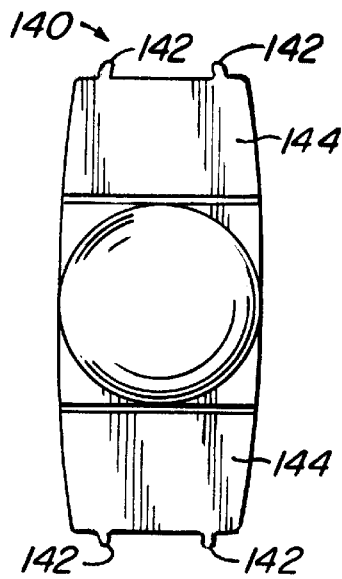
FIG.-19          FIG.-20          FIG.-21

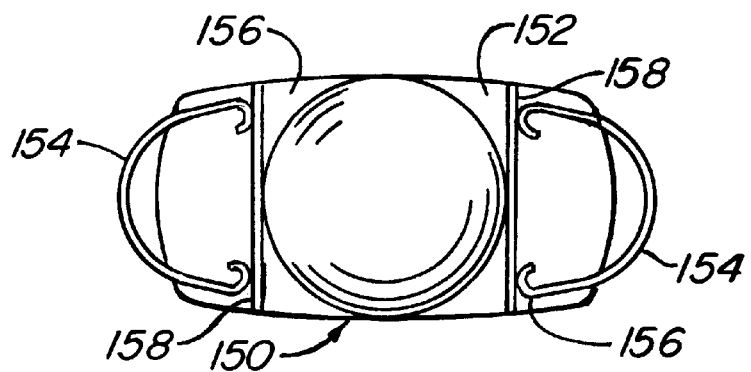
FIG.—22
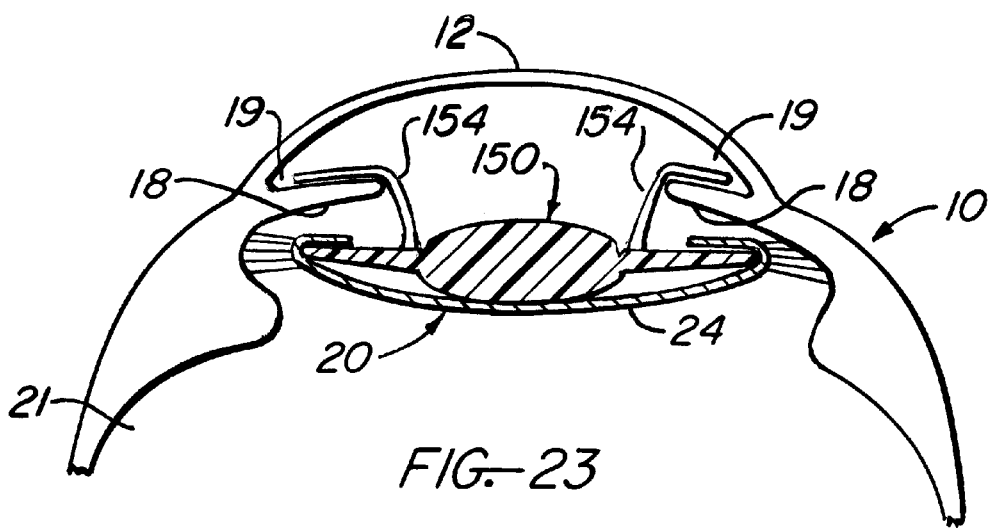
FIG.—23
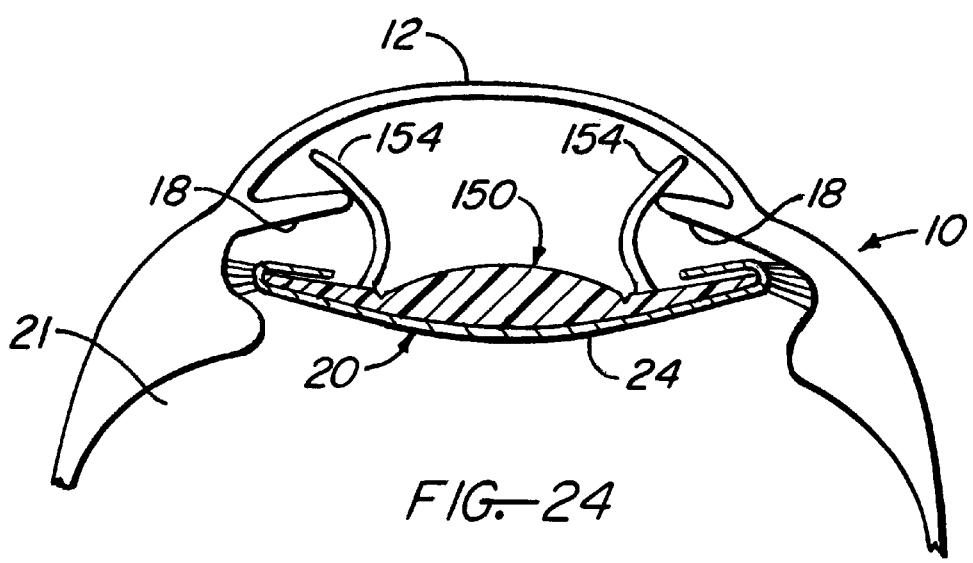
FIG.—24

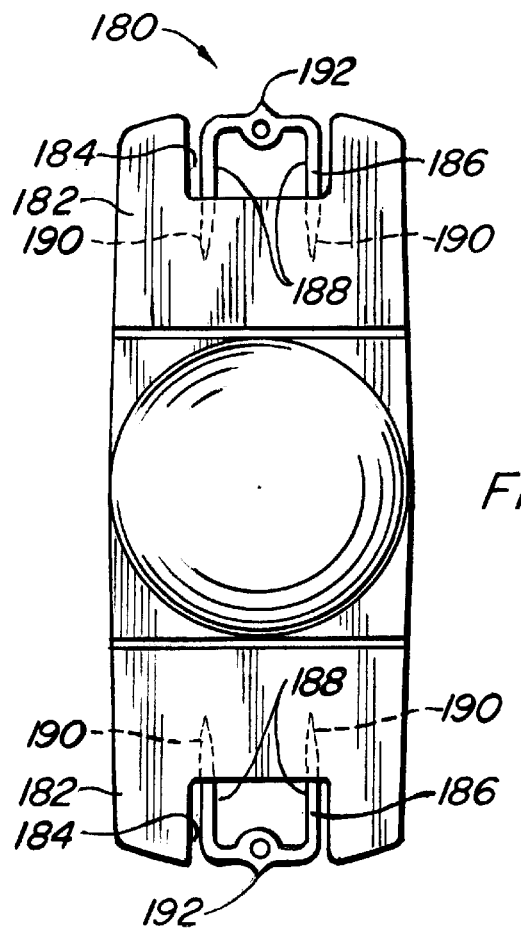
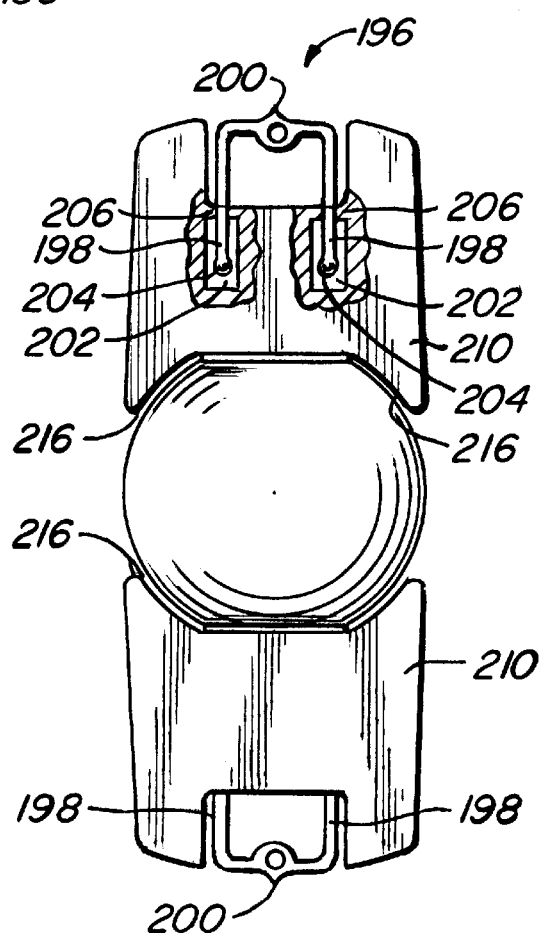

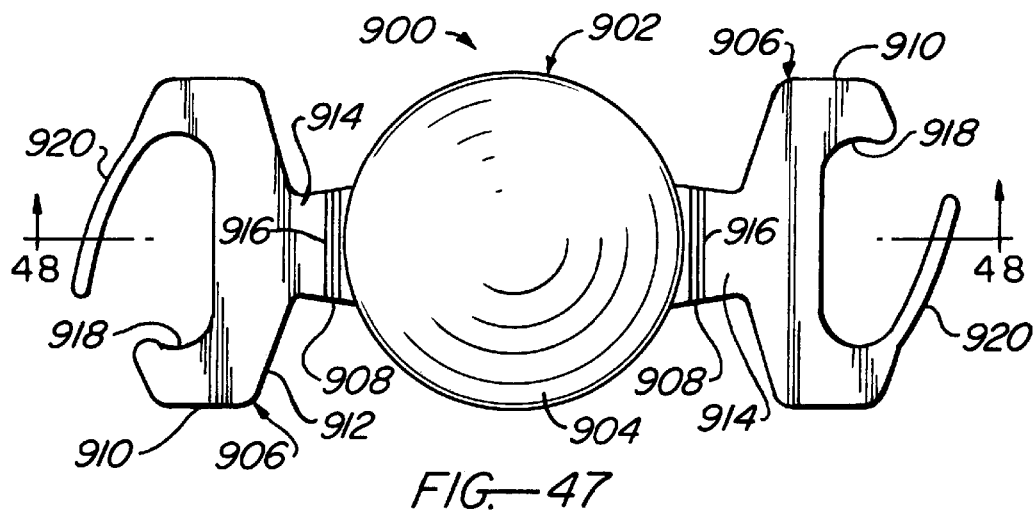
FIG.-47
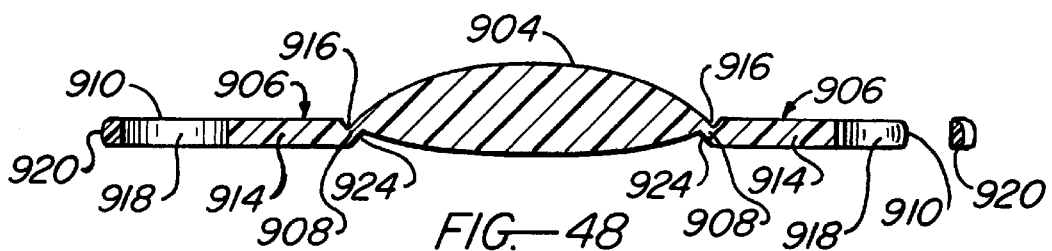
FIG.-48
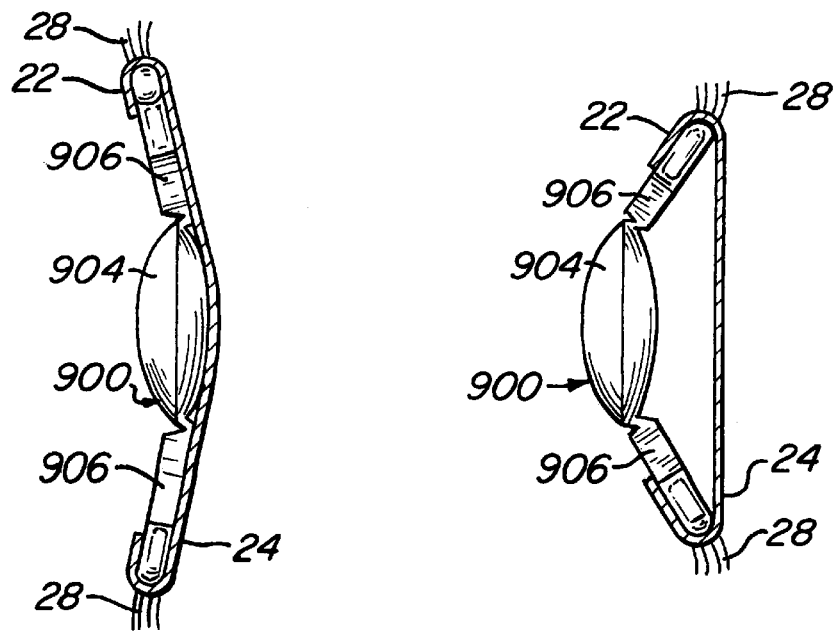
FIG.-49
FIG.-50

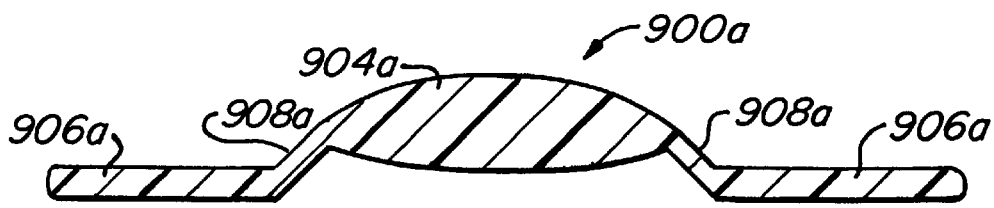
FIG.—51
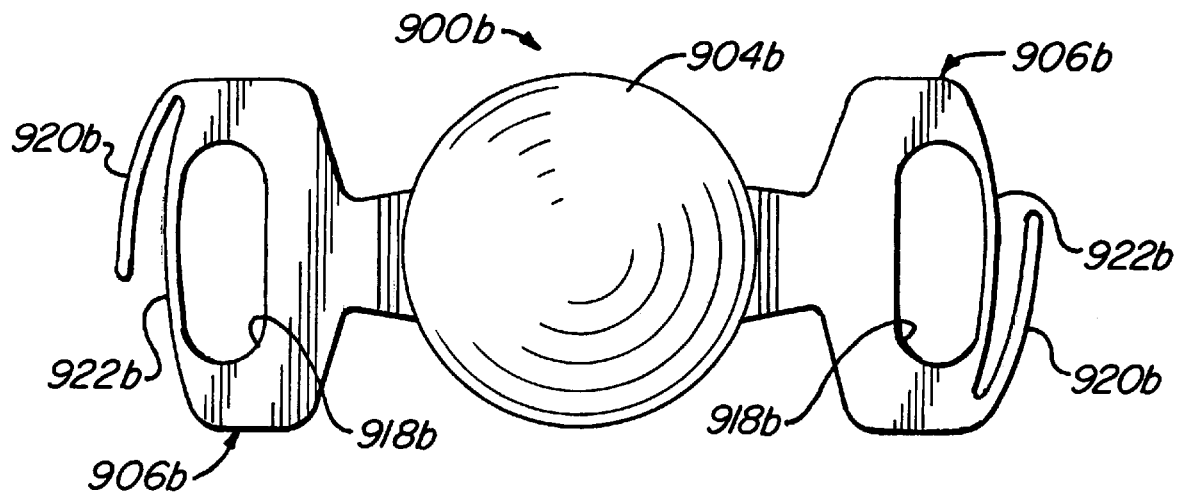
FIG.—52
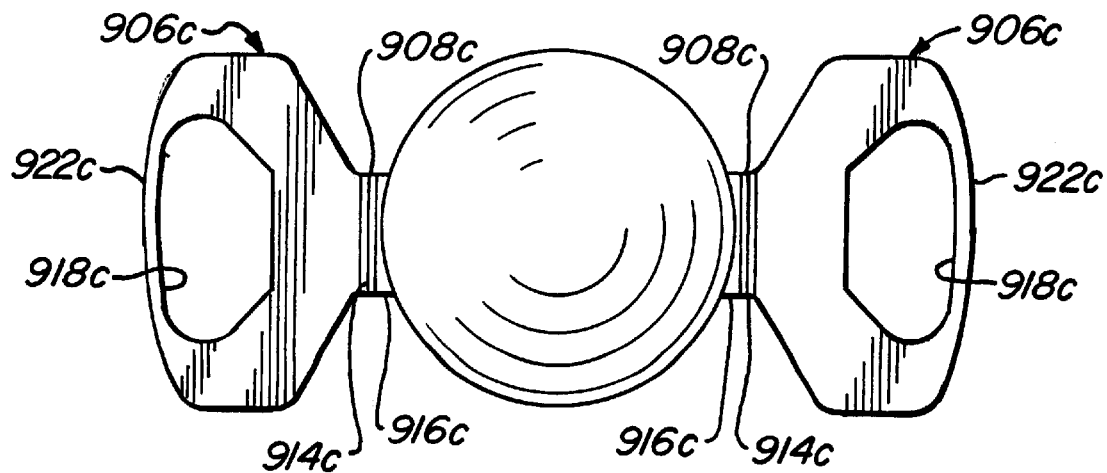
FIG.—53

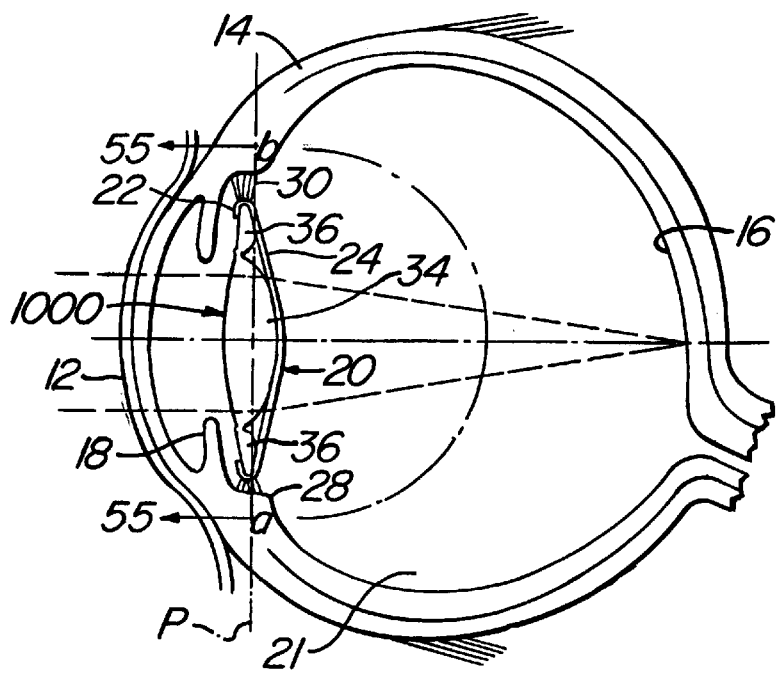
FIG.—54
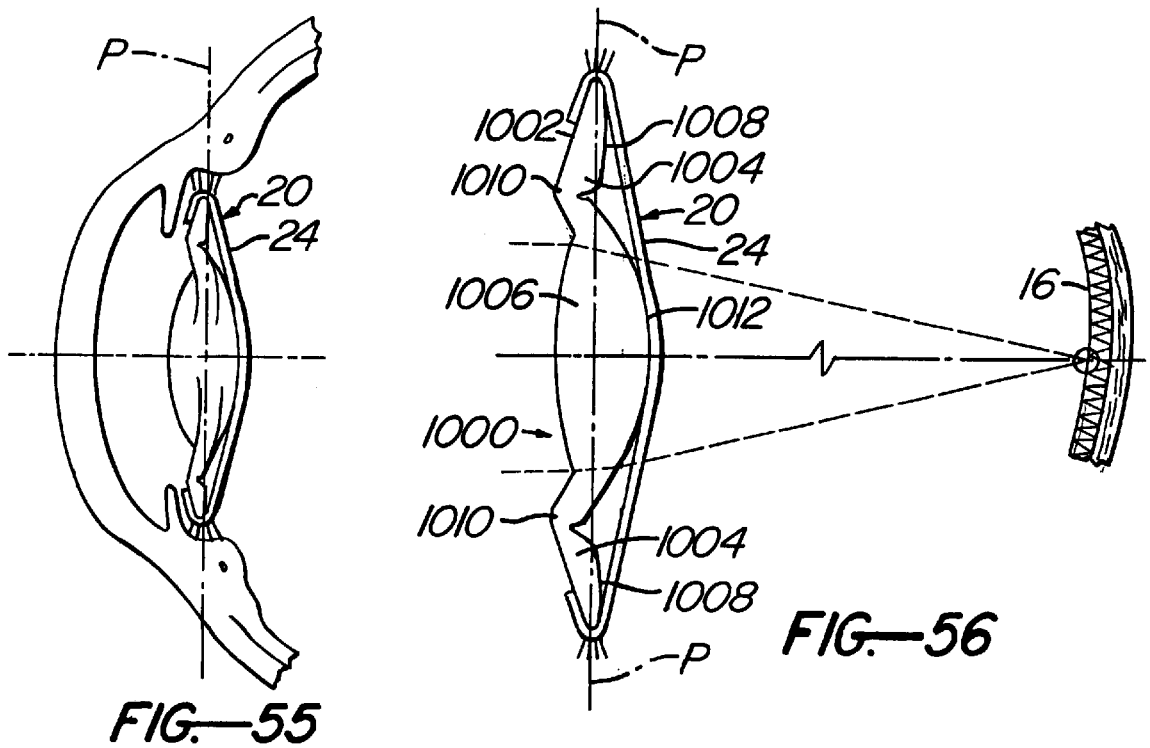
FIG.—55
FIG.—56

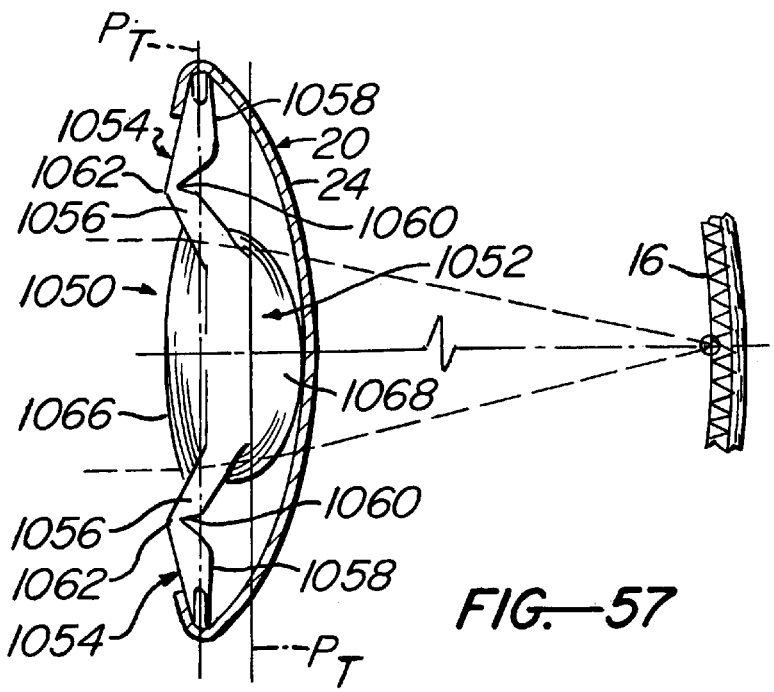
FIG.—57
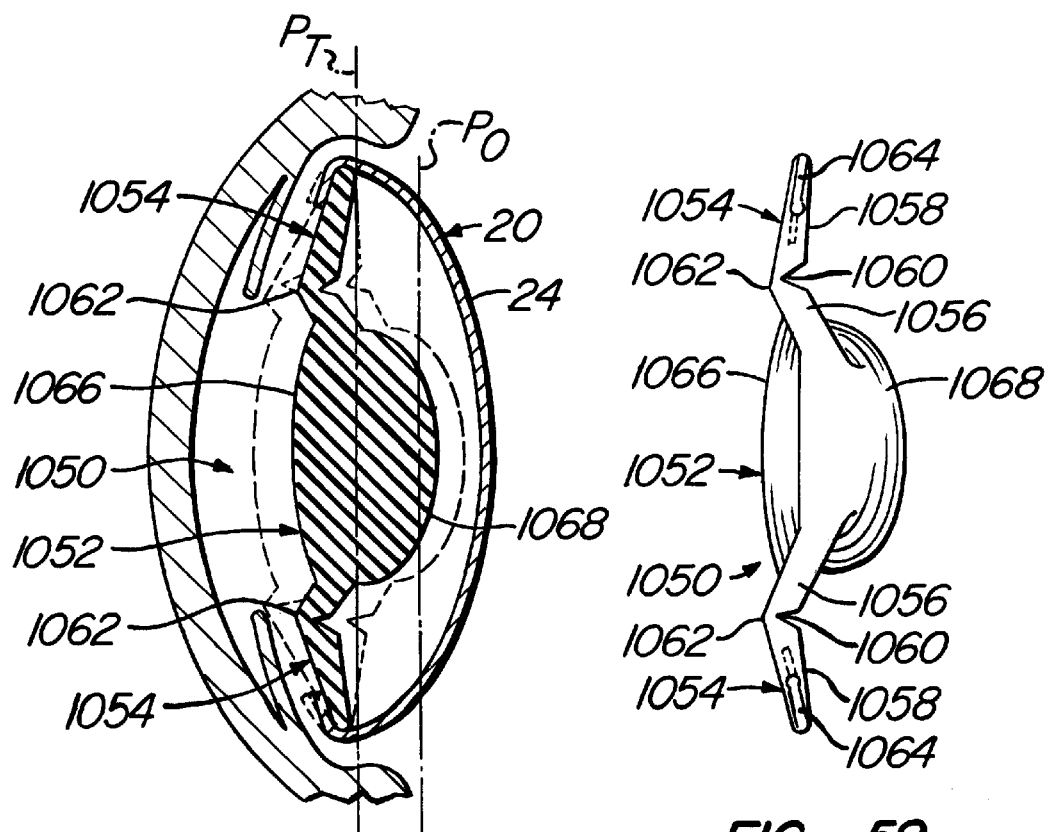
FIG.—58
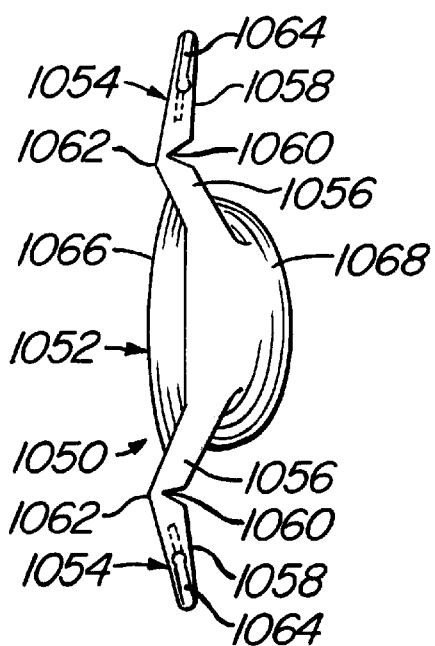
FIG.—59

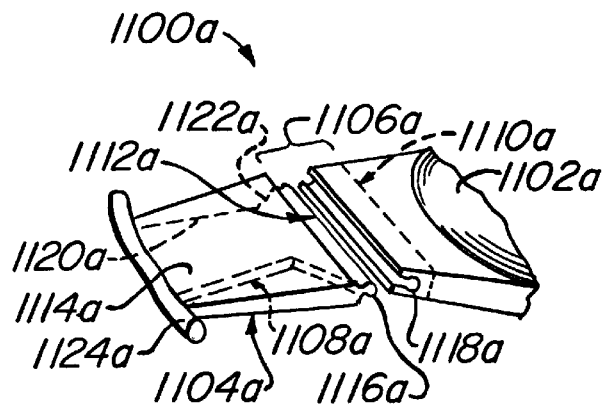
FIG.—60
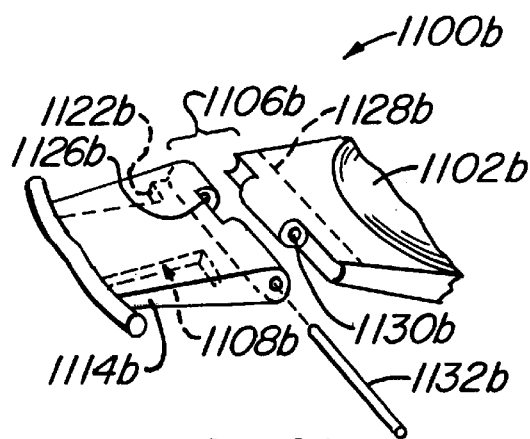
FIG.—61
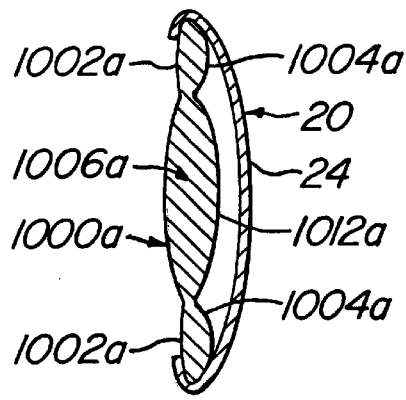
FIG.—62
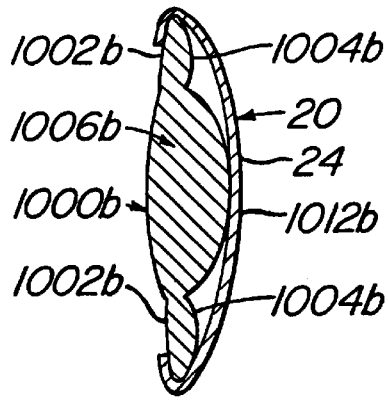
FIG.—63

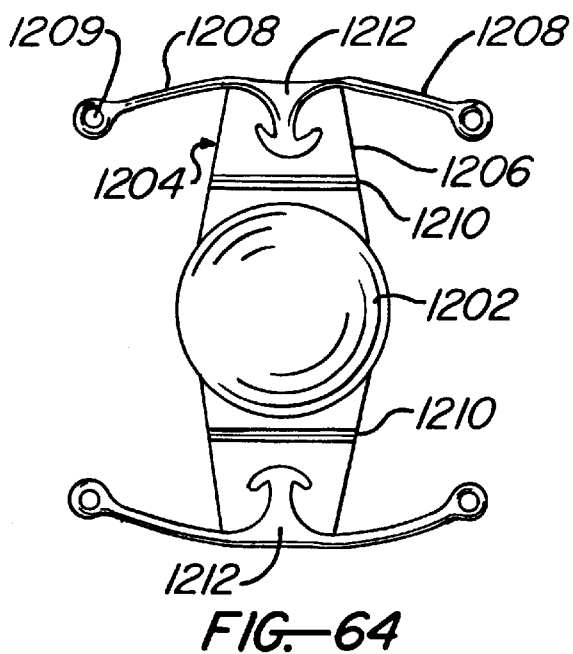
FIG.—64
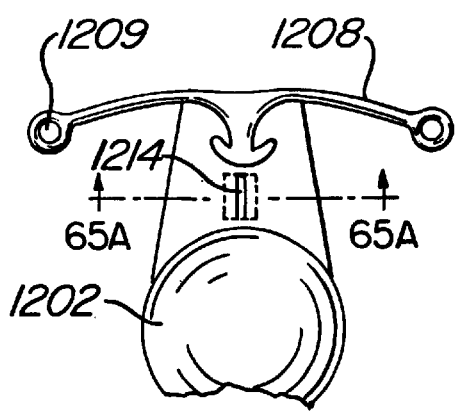
FIG.—65
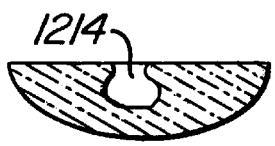
FIG.—65A
FIG.—66A
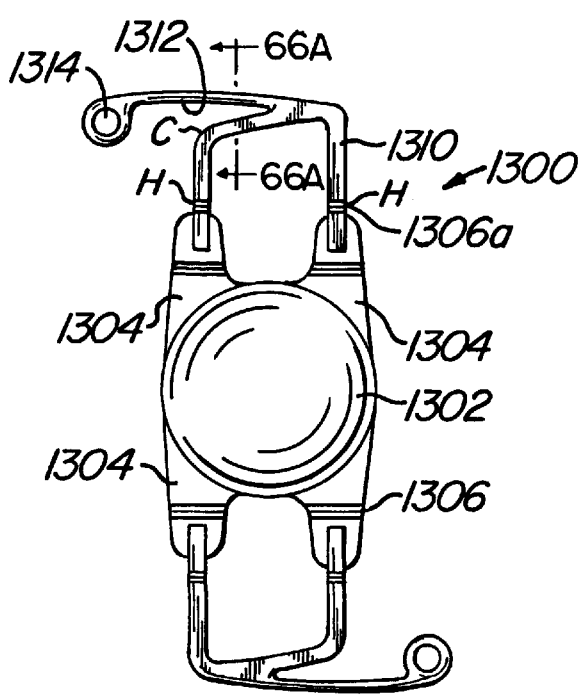
FIG.—66
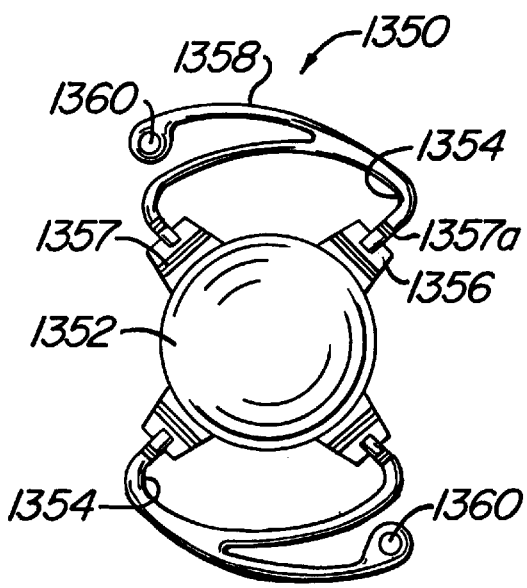
FIG.—67

ACCOMODATING INTRAOCULAR LENS

REFERENCE TO RELATED APPLICATIONS

This application is a continuation-in-part of my application Ser. No. 08/640,118, filed Apr. 30, 1996, now abandoned which is a continuation of Ser. No. 08/500,010 filed Jul. 10, 1995, now abandoned which is a continuation of Ser. No. 08/113,215, filed Aug. 27, 1993, now abandoned which is a continuation-in-part of Ser. No. 08/020,630 now U.S. Pat. No. 5,476,514, which is a continuation-in-part of Ser. No. 07/915,453, filed Jul. 16, 1992 now abandoned, which is a continuation-in-part of Ser. No. 07/515,636, filed Apr. 27, 1990 now abandoned.

BACKGROUND OF THE INVENTION

1. Field of the Invention

This invention relates generally to intraocular lenses and more particularly to novel accommodating intraocular lenses for implantation within the capsular bag of a human eye from which the natural lens matrix has been removed by an extraction procedure which leaves intact within the eye the posterior capsule and an anterior capsule remnant of the natural lens. The invention relates also to a novel method of utilizing the intraocular lenses in a human eye to provide the patient with accommodation capability responsive to normal ciliary muscle action.

2. Prior Art

The human eye has an anterior chamber between the cornea and the iris, a posterior chamber behind the iris containing a crystalline lens, a vitreous chamber behind the lens containing vitreous humor, and a retina at the rear of the vitreous chamber. The crystalline lens of a normal human eye has a lens capsule attached about its periphery to the ciliary muscle of the eye by zonules and containing a crystalline lens matrix. This lens capsule has elastic optically clear anterior and posterior membrane-like walls commonly referred by ophtalmologists as anterior and posterior capsules, respectively. Between the iris and ciliary muscle is an annular crevice-like space called the ciliary sulcus.

The human eye possesses natural accommodation capability. Natural accommodation involves relaxation and constriction of the ciliary muscle by the brain to provide the eye with near and distant vision. This ciliary muscle action is automatic and shapes the natural crystalline lens to the appropriate optical configuration for focussing on the retina the light rays entering the eye from the scene being viewed.

The human eye is subject to a variety of disorders which degrade or totally destroy the ability of the eye to function properly. One of the more common of these disorders involves progressive clouding of the natural crystalline lens matrix resulting in the formation of what is referred to as a cataract. It is now common practice to cure a cataract by surgically removing the cataractous human crystalline lens and implanting an artificial intraocular lens in the eye to replace the natural lens. The prior art is replete with a vast assortment of intraocular lenses for this purpose. Examples of such lenses are described in the following patents: U.S. Pat. Nos. 4,254,509, 4,298,996, 4,842,601, 4,963,148, 4,994,082, 5,047,051.

As is evident from the above patents, intraocular lenses differ widely in their physical appearance and arrangement. This invention is concerned with intraocular lenses of the kind having a central optical region or optic and haptics which extend outward from the optic and engage the interior of the eye in such a way as to support the optic on the axis of the eye. My above-listed patent U.S. Pat. No. 5,047,051, discloses an intraocular lens having a haptic anchor plate, an optic at the longitudinal center of the plate, and resilient haptic loops staked to the ends of the plate.

Up until the late 1980's, cataracts were surgically removed by either intracapsular extraction involving removal of the entire human lens including both its outer lens capsule and its inner crystalline lens matrix, or by extracapsular extraction involving removal of the anterior capsule of the lens and the inner crystalline lens matrix but leaving intact the posterior capsule of the lens. Such intracapsular and extracapsular procedures are prone to certain post-operative complications which introduce undesirable risks into their utilization. Among the most serious of these complications are opacification of the posterior capsule following extracapsular lens extraction, intraocular lens decentration, cystoid macular edema, retinal detachment, and astigmatism.

An improved surgical procedure called anterior capsulotomy was developed to alleviate the above and other post-operative complications and risks involved in intracapsular and extra-capsular cataract extraction. Simply stated, anterior capsulotomy involves forming an opening in the anterior capsule of the natural lens, leaving intact within the eye a capsular bag having an elastic posterior capsule, and anterior capsular remnant or rim about the anterior capsule opening, and an annular sulcus, referred to herein as a capsular bag sulcus, between the anterior capsule remnant and the outer circumference of the posterior capsule. This capsular bag remains attached about its periphery to the surrounding ciliary muscle of the eye by the zonules of the eye. The cataractous natural lens matrix is extracted from the capsular bag through the anterior capsule opening by phacoemulsification and aspiration or in some other way after which an intraocular lens is implanted within the bag through the opening.

A relatively recent and improved form of anterior capsulotomy known as capsulorhexis is essentially a continuous tear circular or round capsulotomy. A capsulorhexis is performed by tearing the anterior capsule of the natural lens capsule along a generally circular tear line substantially coaxial with the lens axis and removing the generally circular portion of the anterior capsule surrounded by the tear line. A continuous tear circular capsulotomy or capsulorhexis, if performed properly, provides a generally circular opening through the anterior capsule of the natural lens capsule substantially coaxial with the axis of the eye and surrounded circumferentially by a continuous annular remnant or rim of the anterior capsule having a relatively smooth and continuous inner edge bounding the opening. When performing a continous tear circular capsulorhexis, however, the anterior rim is often accidentally torn or sliced or otherwise ruptured, or the inner rim edge is nicked or sliced in a manner which renders the rim prone to tearing when the rim is stressed, as it is during fibrosis as discussed below.

Another anterior capsulotomy procedure, referred to as an envelope capsulotomy, involves cutting a horizontal incision in the anterior capsule of the natural lens capsule, then cutting two vertical incisions in the anterior capsule intersecting and rising from the horizontal incision, and finally tearing the anterior capsule along a tear line having an upper upwardly arching portion which starts at the upper extremity of the vertical incision and continues in a downward vertical portion parallel to the vertical incision which extends downwardly and then across the second vertical incision. This procedure produces a generally archway-shaped anterior capsule opening centered on the axis of the eye. The opening is bounded at its bottom by the horizontal incision, at one vertical side by the vertical incision, at its opposite vertical side by the second vertical incision of the anterior capsule, and at its upper side by the upper arching portion of the capsule tear. The vertical incision and the adjacent end of the horizontal incision form a flexible flap at one side of the opening. The vertical tear edge and the adjacent end of the horizontal incision form a second flap at the opposite side of the opening.

A third capsulotomy procedure, referred to as a beer can or can opener capsulotomy, involves piercing the anterior capsule of the natural lens at a multiplicity of positions along a circular line substantially coaxial with the axis of the eye and then removing the generally circular portion of the capsule circumferentially surrounded by the line. This procedure produces a generally circular anterior capsule opening substantially coaxial with the axis of the eye and bounded circumferentially by an annular remnant or rim of the anterior capsule. The inner edge of this rim has a multiplicity of scallops formed by the edges of the pierced holes in the anterior capsule which render the annular remnant or rim prone to tearing radially when the rim is stressed, as it is during fibrosis as discussed below.

Intraocular lenses also differ with respect to their accommodation capability, and their placement in the eye. Accommodation is the ability of an intraocular lens to accommodate, that is to focus the eye for near and distant vision. My U.S. Pat. No. 5,326,347 and certain of the earlier listed patents describe accommodating intraocular lenses. Others of the listed patents describe non-accommodating intraocular lenses. Most non-accommodating lenses have single focus optics which focus the eye at a certain fixed distance only and require the wearing of eye glasses to change the focus. Other non-accommodating lenses have bifocal optics which image both near and distant objects on the retina of the eye. The brain selects the appropriate image and suppresses the other image, so that a bifocal intraocular lens provides both near vision and distant vision sight without eyeglasses. Bifocal intraocular lenses, however, suffer from the disadvantage that each bifocal image represents only about 40% of the available light and the remaining 20% of the light is lost in scatter.

There are four possible placements of an intraocular lens within the eye. These are (a) in the anterior chamber, (b) in the posterior chamber, (c) in the capsular bag, and (d) in the vitreous chamber.

SUMMARY OF THE INVENTION

According to one of its aspects, this invention provides improved accommodating intraocular lenses to be implanted within the capsular bag of a human eye which remains in the eye after removal of the natural matrix from the human lens capsule through an anterior capsule opening created by an anterior capsulotomy and preferably by a capsulorhexis. An improved accommodating intraocular lens according to the invention has a central optic and haptics which extend outward from diametrically opposite sides of the optic and are movable anteriorly and posteriorly relative to the optic. In some described lens embodiments, the haptics are joined at their inner ends to the optic by hinge-like junctions referred to herein as hinges, and the anterior/posterior movement of the haptics involves pivotal movement of the haptics at these hinges. In other described embodiments, the haptics are resiliently flexible, and the anterior/posterior movement of the haptics relative to the optic involves resilient flexing or bending of the haptics. In this regard, it is important to note at the outset that the terms "flex", "flexing", "flexible", and the like are used herein in a broad sense to cover both hinged and resiliently bendable haptics.

Certain of the lens embodiments described herein are referred to as simple plate haptic lenses. These simple plate haptic lenses are intended for use when the capsulotomy procedure utilized in the eye surgery is properly performed and provides an anterior capsule remnant or rim that is not only completely intact and free of splits, tears, and the like at the time of lens implantation but is also likely to remain intact during subsequent fibrosis. Other described lens embodiments are referred to as a plate haptic spring lens. These latter lenses are intended for use in those situations in which the capsulotomy produces an anterior capsular remnant which is not intact or which is not likely to remain intact during fibrosis. Both types of lenses are designed for implantation within a capsular bag of the eye in a position wherein the lens optic is aligned on the axis of the eye with the anterior capsule opening in the bag, and the lens haptics are situated within the capsular bag sulcus in contact with the sulcus wall. The normally posterior side of the lens then faces the elastic posterior capsule of the bag.

The presently preferred lens embodiments of the invention have round optics and haptics joined at their inner ends to opposite edges of the optic by relatively narrow junctions. These junctions occupy only relatively small diametrically opposite edge portions of the optics and leave unobstructed the remaining major circular edge portions of the optic between the junctions. In the preferred lenses described herein, these junctions are hinge junctions about which the haptics are movable anteriorly and posteriorly relative to the optic. These flexible or hinged junctions form a bridge between the optic and the plate haptic which is fixed in position within the anterior and posterior capsules by fibrosis. The bridges are tapered, the widest end being adjacent to the optic. This allows the bridge to slide in and out of the pocket formed by the fibrosed anterior capsular rim and the posterior capsule, and enables the optic to move anteriorly when the plate haptics are subjected to end to end compression.

During a post operative healing period on the order of three weeks, active endodermal cells on the posterior side of the anterior capsular rim cause fusion of the rim to the elastic posterior capsule by fibrosis. Fibrosis occurs about the haptics in such a way that the haptics are effectively "shrink-wrapped" by the capsular bag and form radial pockets between the anterior rim and the posterior capsule. These pockets contain the haptics and act to position and center the lens in the eye. The anterior capsular rim shrinks during fibrosis. This shrinkage combined with shrink-wrapping of the haptics causes endwise compression of the lens in a manner which tends to deflect the center of the lens along the axis of the eye relative to the fixated outer haptic ends. The intact fibrosed capsular rim prevents forward deflection of the lens, so that fibrosis-induced deflection of the lens occurs rearwardly to a position in which the lens presses against the elastic posterior capsule and stretches this capsule rearwardly.

Relaxation of the ciliary muscle during normal use of the eye after completion of fibrosis stretches the capsular bag and the fibrosed anterior capsular rim. The rim is stretched to a taut trampoline-like condition in which the rim deflects the lens rearwardly to and holds the lens in a posterior position. In this position of the lens, which is its distant vision position, the lens optic presses rearwardly against and stretches the elastic posterior capsule. The stretched posterior capsule then exerts a forward bias force on the lens.

The accommodating lenses of the invention are uniquely constructed and arranged to utilize the fibrosed anterior capsular rim, the elastic posterior capsule, the vitreous cavity pressure, and the natural brain-controlled ciliary muscle action of the eye to provide postoperative accommodation for near vision. Thus, when looking at a near object, the brain constricts the ciliary muscle. This relaxes the fibrosed anterior rim, increases vitreous cavity pressure, and compresses the lens endwise in such a way as to effect forward deflection, i.e. accommodation movement, of the lens optic along the axis of the eye to a near vision position. Depending upon the amount of accommodation, accommodation deflection of the lens is produced initially by the increase in vitreous pressure and the forward bias force of the stretched posterior capsule and finally by forward buckling of the lens in response to endwise compression of the lens. Subsequent brain-activated relaxation of the ciliary muscle stretches the capsular bag and the fibrosed anterior capsular rim to return the lens rearwardly toward its distant vision position.

The preferred lens embodiments of the invention have round optics which are sized in diameter to pass through the anterior capsule opening. These preferred lenses are constructed and arranged for anterior accommodation movement of their optics to positions wherein the optics project through the anterior capsule opening to maximize the accommodation range of the lenses.

According to another important aspect of the invention, the ciliary muscle is paralyzed in its relaxed state at the start of surgery and is maintained in this relaxed state during both surgery and post-operative fusion of the anterior capsular remnant or rim to the posterior capsule by fibrosis. The ciliary muscle is thus relaxed by introducing a ciliary muscle relaxant (i.e. a cycloplegic) into the eye. While various cycloplegics may be used, the preferred cycloplegic is atropine because of its relatively long effective period compared to other cycloplegics. The cycloplegic is initially introduced into the eye at the start of surgery to dilate the pupil and paralyze the ciliary muscle in its relaxed state. After surgery, cycloplegic drops are periodically introduced into the eye by the patient during a postoperative healing period of sufficient duration (normally about two to three weeks) to maintain the ciliary muscle in its relaxed state until fibrosis is complete. This drug-induced relaxation of the ciliary muscle prevents contraction of the muscle and immobilizes the capsular bag during fibrosis. By this means, the lens is fixed in position within the eye relative to the retina for distance vision. When the cycloplegic effect wears off and the ciliary muscle can contract again, the contraction causes end to end compression on the plates thus moving the optic anteriorly for near vision. If the ciliary muscle was not maintained in its relaxed state, the muscle would undergo essentially normal brain-induced vision accommodation contraction and relaxation during fibrosis. This ciliary muscle action during fibrosis would not only result in improper formation of the haptic pickets in the fibrose tissue, but also ciliary muscle contraction during fibrosis would compress the capsular bag radially and the lens endwise in such a way as to very likely dislocate the lens from its proper position in the bag.

An accommodating lens according to the invention may have a normal unstressed configuration, such that when deflected from its normal unstressed configuration, the lens develops internal elastic strain energy forces which bias the lens toward its normal unstressed configuration in a manner which aids accommodation. The lens may be generally flat, anteriorly arched, or posteriorly arched in this normal unstressed configuration. One disclosed embodiment of the lens includes auxiliary springs for aiding lens accommodation. Some disclosed lens embodiments have integral fixation means at the haptic ends around which fibrosis of the anterior rim of the capsular bag occurs to fix the lens against dislocation in the eye. Other disclosed embodiments have fixation elements from which the lens proper is separable to permit later removal of the lens for repair or correction and replacement of the lens in its exact original position within the eye.

As noted earlier, the simple plate haptic lens of the invention is designed for use when the anterior capsulotomy performed on the eye provides an anterior capsular remnant or rim that remains intact and circumferentially continuous throughout fibrosis. The plate haptic spring lenses are designed for use when the anterior capsular remnant or rim of the capsular bag is ruptured, that is cut or torn, or is liable to become so during fibrosis. A ruptured capsular rim may be produced in different ways. For example, improper performance of a continuous tear circular capsulotomy, or capsulorhexis, may result in accidental cutting or tearing of the anterior rim. A beer can or can opener capsulotomy, on the other hand, produces an anterior capsular rim which is not intact and has an inner scalloped edge having stress-inducing regions that render the rim very prone to tearing during surgery or subsequent fibrosis. An envelope capsulotomy inherently produces an anterior capsular remnant which is ruptured and not intact.

A ruptured anterior capsular remnant or rim may preclude utilization of a simple plate haptic lens of the invention for the following reasons. A ruptured rim may not firmly retain the lens haptics in the sulcus of the capsular bag during fibrosis, thereby rendering the lens prone to decentration and/or posterior or anterior dislocation. A ruptured capsular rim may be incapable of assuming the taut trampoline-like condition of a non-ruptured rim. If so, a ruptured capsular rim is incapable of effecting full posterior deflection of a plate haptic lens to a distant viewing position against the posterior capsule during and after fibrosis. In fact, a ruptured capsular rim may permit anterior deflection of the lens. In either case, since the power of the lens is selected for each individual patient and is dependent upon their spectacle power, and since good vision without glasses requires the lens optic to be at precisely the correct distance from the retina, a simple plate haptic lens of the invention may not be acceptable for use with a ruptured anterior capsular remnant or rim.

The accommodating plate haptic spring lenses of the invention are designed for use when the anterior capsular remnant or rim of the capsular bag is ruptured. These plate haptic spring lenses are similar to the simple plate haptic lenses but have resilient springs, such as spring loops, at the ends of the plate haptics. When a plate haptic spring lens is implanted in a capsular bag, the haptic springs press outward against the wall of the capsular bag sulcus to fixate the lens in the bag during fibrosis. Fibrosis occurs about the springs in such a way as to effect fusion of the ruptured anterior remnant to the posterior capsule, firm fixation of the the springs and hence the haptics in the bag, and posterior deflection of the lenses against the elastic posterior capsule during fibrosis. Brain-induced constriction and relaxation of the ciliary muscle after fibrosis with a ruptured capsular rim effects accommodation of the plate haptic spring lens in much the same way as occurs with the simple plate haptic lens and an intact non-ruptured capsular rim.

While the plate haptic spring lenses of the invention are designed for use with a ruptured anterior capsular remnant or rim, these lenses can also be utilized with an intact rim. A plate haptic spring lens also compensates for improper lens placement in the eye with one end of the lens situated in the capsular bag and the other end of the lens situated in the ciliary sulcus of the eye. In this regard, an advantage of the plate haptic spring lenses of the invention over the simple plate haptic lenses resides in the fact that the spring lenses eliminate the need to have on hand in the operating room both a simple plate haptic lens for use with an intact capsular rim and a plate haptic spring lens as a substitute for the plate haptic lens in the event the rim is ruptured during surgery.

Another advantage of the plate haptic spring lenses over the simple plate haptic lenses of the invention resides in the fact that the haptic spring lenses permit an optic of larger diameter than those of simple plate haptic lenses whose optic diameters will normally be restricted to the range of 4–7 mm. Thus, the haptic spring lenses rely on the haptic springs rather than the capsular remnant or rim to retain the lenses in position during fibrosis. As a consequence, these lenses may be used with a capsular remnant or rim of reduced radial width or a capsular rim which is slit or torn, both of which rim types provide an anterior capsule opening of larger effective size than those possible with a simple plate haptic lens. A larger anterior capsule opening, in turn, permits a larger optic diameter which offers certain opthalmological benefits. According to one aspect of this invention, such a large opening is provided after fibrosis is complete by using a laser to slit the anterior capsular rim radially or cut the rim circumferentially to enlarge the opening.

A further aspect of the invention concerns a novel method of utilizing an accommodating lens of the invention to provide accommodation in a human eye whose natural lens matrix has been removed from the lens capsule by a procedure involving anterior capsulotomy of the natural lens. The method may be utilized to replace a natural lens from which a cataract has been removed and to correct a refractive error in the eye of a patient who previously wore glasses in order to enable the patient to see well without glasses. For example, the invention can can be utilized to correct refractive errors and restore accommodation to persons in their mid-40's who require reading glasses or bifocals for near vision by replacing the clear non-cataractous crystalline lens matrix of their eyes with an accomodating intraocular lens according to the invention. According to the method of utilizing a plate haptic spring lens of the invention, the anterior capsular remnant or rim of the capsular bag is slit radially or cut to enlarge the anterior capsule opening after fibrosis is complete to permit the use of a lens with a relatively large diameter optic larger than 6 or 7 mm.

BRIEF DESCRIPTION OF THE DRAWINGS

FIG. 1 is a section through a human eye from which the natural lens matrix has been removed by a surgical procedure involving anterior capsulotomy, such as capsulor-hexis, of the natural lens, and illustrating an accommodating simple plate haptic accommodating lens according to this invention implanted within the capsular bag of the eye;

FIG. 1A is a section through a normal human eye;

FIG. 2 is an anterior side view of the intraocular lens of FIG. 1;

FIG. 3 is a section taken on line 3—3 in FIG. 2;

FIG. 4 is a section taken on line 4—4 in FIG. 1;

FIGS. 5–8 illustrate the manner in which the intraocular lens of FIGS. 1–4 is utilized in the eye of FIG. 1 to provide accommodation;

FIGS. 9–12 are sections, similar to FIG. 3, through modified accommodating intraocular lenses according to the invention having alternative optical shapes;

FIG. 13 is a section similar to FIG. 3 through a modified accommodating intraocular lens according to the invention illustrating the lens in its normal unstressed configuration;

FIG. 14 is a section similar to FIG. 16, illustrating the lens in its distant vision position;

FIG. 15 is a section through a modified accommodating intraocular lens according to the invention having an anteriorly displaced optic;

FIG. 16 is an anterior side view of a modified accommodating intraocular lens according to the invention having integral fixation means for fixing the lens in the capsular bag of the eye;

FIG. 17 is a section taken on line 17—17 in FIG. 16;

FIGS. 18–21 are anterior side views of modified accommodating intraocular lenses according to the invention having alternative integral fixation means for fixing the lenses in the capsular bag of the eye;

FIG. 22 is an anterior side view of a modified accommodating intraocular lens according to the invention having springs for aiding accommodation;

FIG. 23 illustrates the lens of FIG. 22 implanted within the capsular bag of a human eye like that in FIG. 1, and showing the lens in the position which the lens occupies immediately after surgery as well as after a certain degree of accommodation;

FIG. 24 is a view similar to FIG. 23 showing the lens in its posterior distant vision position;

FIGS. 25–30 are anterior side views of modified accommodating intraocular lenses according to the invention having separate fixation means for fixing the lenses in the capsular bag of a human eye like that in FIG. 1;

FIG. 47 is a plan view of the anterior side of a presently preferred accommodating lens according to the invention;

FIG. 48 is a section taken on line 48—48 in FIG. 47;

FIG. 49 illustrates the lens of FIG. 47 implanted within the capsular bag of an eye and shows the lens in its posterior distant vision position;

FIG. 50 is a view similar to FIG. 49 showing the lens at or near the forward limit of its accommodation;

FIG. 51 is a section similar to FIG. 48 through a modified accommodating lens according to the invention;

FIG. 52 is a view similar to FIG. 47 of a further modified accommodating lens according to the invention;

FIG. 53 is a view similar to FIG. 47 of yet a further modified accommodating lens according to the invention;

FIG. 54 is a view showing an anteriorly biased accommodating intraocular lens of the invention in its posterior distant vision position within the eye after completion of fibrosis following surgery;

FIG. 55 is an enlargement of the area encircled by the arrow 55—55 in FIG. 54;

FIG. 56 is a further enlarged view of an intraocular lens according to the invention and natural capsular bag, showing incoming light rays focused on the retina of the eye;

FIGS. 57 and 58 are sectional views showing a preferred anteriorly biased accommodating intraocular lens according to the invention, which provides increased accommodation amplitude and increased diopters of accommodation, FIG. 58 showing the preferred intraocular lens in solid lines in a mid-range position of accommodation, in phantom lines in its posterior distant vision position of accommodation, and in dashed lines in its anterior near vision position of accommodation;

FIG. 59 is an edge view of the lens in FIG. 58;

FIG. 60 is an exploded fragmentary perspective view of a modified accommodating intraocular lens according to the invention having pivotally hinged haptics;

FIG. 61 is a view similar to FIG. 60 but showing a modified haptic hinge arrangement including reinforcing hinge inserts, and a modified hinge arrangement;

FIGS. 62 and 63 are views similar to the anterior portion of FIG. 56 but illustrating two modified anteriorly biased accommodating intraocular lenses according to the invention in their posterior distant vision positions within the capsular bag of the eye;

FIG. 64 is a plan view of an improved accommodating intraocular lens according to the invention having extended haptic portions in the form of resiliently bendable fingers defined by haptic inlays;

FIG. 65 illustrates an embodiment similar to that of FIG. 64 and including a depressed pocket defined in a haptic for accommodating a drug;

FIG. 65A is a sectional view taken at line 65A—65A in FIG. 65;

FIG. 66 is a plan view of another embodiment of the invention wherein pairs of haptics extend oppositely from an optic, a loop extends outwardly between each pair of haptics, and an arm extends generally transversely of each loop with an end protuberance defining an opening;

FIG. 66A is a sectional view taken at line 66A—66A in FIG. 66; and

FIG. 67 shows another embodiment of the invention wherein haptics extend in spaced relation radially from an optic, and two loops extend outwardly between respective pairs of haptics, with an arm extending generally transversely of the loops and having protuberances with openings at their outer ends.

DESCRIPTION OF THE PREFERRED EMBODIMENTS

Figure 25:
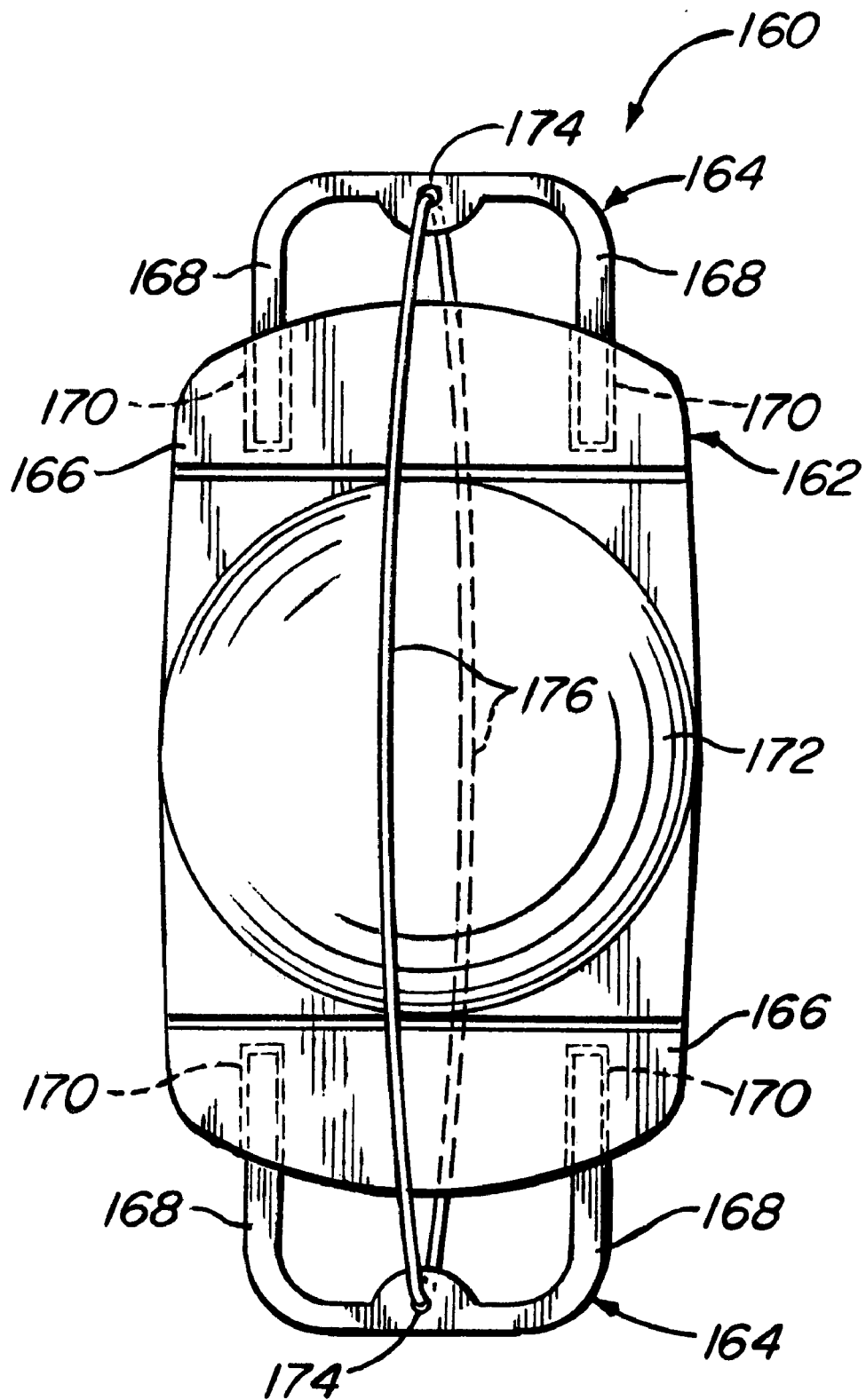

Turning now to these drawings and first to FIGS. 1 and 1A, there is illustrated a human eye 10 from which the natural crystalline lens matrix was previously removed by a surgical procedure involving an anterior capsulotomy, in this case a continuous tear circular tear capsulotomy, or capsulorhexis. The natural lens comprises a lens capsule having elastic anterior and posterior walls A and P, respectively, which are referred to by ophthalmologists and herein as anterior and posterior capsules, respectively. The natural lens capsule (FIG. 1A) contains a normally optically clear crystalline lens matrix M. In many individuals, this lens matrix becomes cloudy with advancing age and forms what is called a cataract. It is now common practice to restore a cataract patient's vision by removing the cataract from the natural lens and replacing the lens matrix by an artificial intraocular lens.

As mentioned earlier, continous tear circular capsulotomy, or capsulorhexis, involves tearing the anterior capsule A along a generally circular tear line in such a way as to form a relatively smooth-edged circular opening in the center of the anterior capsule. The cataract is removed from the natural lens capsule through this opening. After completion of this surgical procedure, the eye includes an optically clear anterior cornea 12, an opaque sclera 14 on the inner side of which is the retina 16 of the eye, an iris 18, a capsular bag 20 behind the iris, and a vitreous cavity 21 behind the capsular bag filled with the gel-like vitreous humor. The capsular bag 20 is the structure of the natural lens of the eye which remains intact within the eye after the continous tear circular tear capsulorhexis has been performed and the natural lens matrix has been removed from on the natural lens.

The capsular bag 20 includes an annular anterior capsular remnant or rim 22 and an elastic posterior capsule 24 which are joined along the perimeter of the bag to form an annular crevice-like capsular bag sulcus 25 between rim and posterior capsule. The capsular rim 22 is the remnant of the anterior capsule of the natural lens which remains after capsulorhexis has been performed on the natural lens. This rim circumferentially surrounds a central, generally round anterior opening 26 (capsulotomy) in the capsular bag through which the natural lens matrix was previously removed from the natural lens. The capsular bag 20 is secured about its perimeter to the ciliary muscle of the eye by zonules 30.

Natural accommodation in a normal human eye having a normal human crystalline lens involves automatic contraction or constriction and relaxation of the ciliary muscle of the eye by the brain in response to looking at objects at different distances. Ciliary muscle relaxation, which is the normal state of the muscle, shapes the human crystalline lens for distant vision. Ciliary muscle contraction shapes the human crystalline lens for near vision. The brain-induced change from distant vision to near vision is referred to as accommodation.

Implanted within the capsular bag 20 of the eye 10 is an accommodating intraocular lens 32 according to this invention which replaces and performs the accommodation function of the removed human crystalline lens. Lens 32 is referred to in places as a simple plate haptic lens to distinguish it from the later described plate haptic spring lens of the invention. As mentioned earlier and will become readily understood as the description proceeds, the accommodating intraocular lens may be utilized to replace either a natural lens which is virtually totally defective, such as a cataractous natural lens, or a natural lens that provides satisfactory vision at one distance without the wearing of glasses but provides satisfactory vision at another distance only when glasses are worn. For example, the accommodating intraocular lens of the invention can be utilized to correct refractive errors and restore accommodation for persons in their mid-40's who require reading glasses or bifocals for near vision.

Intraocular lens 32 comprises a body 33 which may be formed of relatively hard material, relatively soft flexible semi-rigid material, or a combination of both hard and soft materials. Examples of relatively hard materials which are suitable for the lens body are methyl methacrylate, polysulfones, and other relatively hard biologically inert optical materials. Examples of suitable relatively soft materials for the lens body are silicone, hydrogels, thermolabile materials, and other flexible semi-rigid biologically inert optical materials.

The lens body 33 has a generally rectangular shape and includes a central optical zone or optic 34 and plate haptics 36 extending from diametrically opposite edges of the optic. The haptics have inner ends joined to the optic and opposite outer free ends. The haptics 36 are movable anteriorly and posteriorly relative to the optic 34, that is to say the outer ends of the haptics are movable anteriorly and posteriorly relative to the optic. The particular lens embodiment illustrated is constructed of a resilient semi-rigid material and has flexible hinges 38 which join the inner ends of the haptics to the optic. The haptics are relatively rigid and are flexible about the hinges anteriorly and posteriorly relative to the optic. These hinges are formed by grooves 40 which enter the anterior side of the lens body and extend along the inner ends of the haptics. The haptics 36 are flexible about the hinges 38 in the anterior and posterior directions of the optic. The lens has a relatively flat unstressed configuration, illustrated in FIGS. 2 and 3, wherein the haptics 36 and their hinges 38 are disposed in a common plane transverse to the optic axis of the optic 34. Deformation of the lens from this unstressed configuration by anterior or posterior deflection of the haptics about their hinges 38 creates in the hinges elastic strain energy forces which bias the lens to its unstressed configuration. If the lens is constructed of a relatively hard optic material, it may be necessary to replace the flexible hinges 38 by pivotal hinges of some kind. In a later described lens embodiment of the invention, the haptic hinges are eliminated, and the haptics are made flexible throughout their length.

The accommodating intraocular lens 32 is implanted within the capsular bag 20 of the eye 10 in the position shown in FIGS. 1 and 5. When implanting the lens in the bag, the ciliary muscle 28 of the eye is maintained in its relaxed state in which the muscle stretches the capsular bag 20 to its maximum diameter. The lens is inserted into the bag through the anterior capsule opening 26 and placed in the position shown in FIGS. 1 and 4. In this position, the lens optic 34 is aligned on the axis of the eye with the opening 26, the posterior side of the lens faces the elastic posterior capsule 24 of the bag, and the outer ends of the lens haptics 36 are situated within the sulcus 25 at the radially outer perimeter of the bag. The overall length of the lens substantially equals the inner diameter (10–11 mm) of the stretched capsular bag so that the lens fits snugly within the stretched capsular bag with the outer ends of the haptics in contact with the inner perimeter of the bag, as shown. This prevents decentration of the lens and thereby permits the optic 34 to be smaller such that it can move forward inside the capsular rim during the later described accommodation.

During a post-operative healing period on the order of two to three weeks following surgical implantation of the lens 32 in the capsular bag 20, epithelial cells under the anterior capsular rim 22 of the bag cause fusion of the rim to the posterior capsule 24 by fibrosis. This fibrosis occurs around the lens haptics 36 in such a way that the haptics are "shrink-wrapped" by the capsular bag 20, and the haptics form pockets 42 in the fibrosed material F (FIGS. 4 and 6–8). These pockets cooperate with the lens haptics to position and center the lens in the eye. In order to insure proper formation of the haptic pockets 42 and prevent dislocation of the lens by ciliary muscle contraction during fibrosis, sufficient time must be allowed for fibrosis to occur to completion without contraction of the ciliary muscle 28 from its relaxed state. According to an important aspect of this invention, this is accomplished by introducing a ciliary muscle relaxant (cycloplegic) into the eye before surgery to dilate the pupil and paralyze the ciliary muscle in its relaxed state and having the patient periodically administer cycloplegic drops into the eye during a post-operative period of sufficient duration (two to three weeks) to permit fibrosis to proceed to completion without contraction of the ciliary muscle. The cycloplegic maintains the ciliary muscle 28 in its relaxed state in which the capsular bag 20 is stretched to its maximum diameter and immobilized, and the anterior capsular rim 22 is stretched to a taut trampoline-like condition or position. The rim fibroses from this taut condition. The cycloplegic passes through the cornea of the eye into the fluid within the eye and then enters the ciliary muscle from this fluid. While other cycloplegics may be used, atropine is the preferred cycloplegic because of its prolonged paralyzing effect compared to other cycloplegics. One drop of atropine, for example may last for two weeks. However, to be on the safe side, patients may be advised to place one drop of atropine in the eye every day during the fibrosis period.

The capsular rim 22 shrinks during fibrosis and thereby shrinks the capsular bag 20 slightly in its radial direction. This shrinkage combined with shrink wrapping of the lens haptics 36 produces some opposing endwise compression of the lens which tends to buckle or flex the lens at its hinges 38 and thereby move the lens optic 34 along the axis of the eye. Unless restrained, this flexing of the lens might occur either forwardly or rearwardly. The taut anterior capsular rim 22 pushes rearwardly against and thereby prevents forward flexing of the lens. This fibrosis-induced compression of the lens is not sufficient to interfere with proper formation of the haptic pockets in the fibrosed tissue or cause dislocation of the lens. Accordingly, endwise compression of the lens by fibrosis aided by the rearward thrust of the taut capsular rim against the lens haptics 36 causes rearward flexing of the lens from its initial position of FIGS. 1 and 5 to its position of FIG. 6. The lens haptics 36 are made sufficiently rigid that they will not be bent or bowed by the forces of fibrosis. At the conclusion of fibrosis, the lens occupies its posterior position of FIG. 6 wherein the lens presses rearwardly against the elastic posterior capsule 24 and stretches this capsule rearwardly. The posterior capsule then exerts a forward elastic bias force on the lens. This posterior position of the lens is its distant vision position.

Ciliary muscle induced flexing of the lens 32 during fibrosis can be resisted or prevented by placing sutures within the hinge grooves 40. Removal of these sutures after completion of fibrosis may be accomplished by using sutures that are either absorbable in the fluid within the eye or by using sutures made of a material, such as nylon, which can be removed by a laser.

Natural accommodation in a normal human eye involves shaping of the natural crystalline lens by automatic contraction and relaxation of the ciliary muscle of the eye by the brain to focus the eye at different distances. Ciliary muscle relaxation shapes the natural lens for distant vision. Ciliary muscle contraction shapes the natural lens for near vision.

The accommodating intraocular lens 32 is uniquely constructed to utilize this same ciliary muscle action, the fibrosed capsular rim 22, the elastic posterior capsule 24, and the vitreous pressure within the vitreous cavity 21 to effect accommodation movement of the lens optic 34 along the optic axis of the eye between its distant vision position of FIG. 6 to its near vision position of FIG. 8. Thus, when looking at a distant scene, the brain relaxes the ciliary muscles 28. Relaxation of the ciliary muscle stretches the capsular bag 20 to its maximum diameter and its fibrosed anterior rim 22 to the taut trampoline-like condition or position discussed above. The taut rim deflects the lens rearwardly to its posterior distant vision position of FIG. 6 in which the elastic posterior capsule 24 is stretched rearwardly by the lens and thereby exerts a forward bias force on the lens. When looking at a near scene, such as a book when reading, the brain constricts or contracts the ciliary muscle. This ciliary muscle contraction has the three-fold effect of increasing the vitreous cavity pressure, relaxing the capsular bag 20 and particularly its fibrosed capsular rim 22, and exerting opposing endwise compression forces on the ends of the lens haptics 36 with resultant endwise compression of the lens. Relaxation of the capsular rim permits the rim to flex forwardly and thereby enables the combined forward bias force exerted on the lens by the rearwardly stretched posterior capsule and the increased vitreous cavity pressure to push the lens forwardly in an initial accommodation movement from the position of FIG. 6 to the intermediate accommodation position of FIG. 7.

In this intermediate accommodation position, the lens is substantially flat, and the ends of the lens haptics and their hinges 38 are disposed substantially in a common plane normal to the axis of the eye. During the initial accommodation, the lens arches rearwardly so that endwise compression of the lens by ciliary muscle contraction produces a rearward buckling force on the lens which resists the initial accommodation. However, the increased vitreous cavity pressure and the forward bias force of the stretched posterior capsule are sufficient to overcome this opposing rearward buckling force and effect forward accommodation movement of the lens to and at least just slightly beyond the intermediate position of FIG. 7. At this point, endwise compression of the lens by the contracted ciliary muscle produces a forward buckling force on the lens which effects final accommodation of the lens beyond the intermediate position of FIG. 7 to the near vision position of FIG. 8. Subsequent brain-induced relaxation of the ciliary muscle 28 in resonse to looking at a distant scene reduces the vitreous cavity pressure, stretches the capsular bag 20 to its maximum diameter, and restores the anterior capsular rim 22 to its taut trampoline-like condition to effect return of the lens to its distant viewing position of FIG. 6. During accommodation, the lens optic 34 moves along the axis of the eye toward and away from the retina 16. The power of the optic is selected by the brain to sharply focus incoming light rays on the retina throughout the range of this accommodation movement.

The lens haptics 36 flex at their hinges 38 with respect to the lens optic 34 during accommodation. Any elastic strain energy forces developed in the hinges during this flexing produces additional anterior and/or posterior forces on the lens. For example, assume that the lens is relatively flat, i.e., that the lens haptics 36 lie in a common plane as shown in FIG. 1, in the normal unstressed state of the lens. In this case, posterior deflection of the lens from its position of FIG. 1 to its distant vision position of FIG. 6 creates elastic strain energy forces in the hinges 38 which urge the lens forwardly back to its unstressed position of FIGS. 1 and thus aid the above discussed initial accommodation of the lens in response to contraction of the ciliary muscle. Final accommodation flexing of the lens from its intermediate position of FIG. 7 to its near vision position of FIG. 8 creates elastic strain energy forces in the hinges 38 which urge the lens rearwarly toward its unstressed position and thus aid initial return of the lens from its near vision position to its distant vision position in response to relaxation of the ciliary muscle. The lens may be designed to assume some other normal unstressed position, of course, in which case any elastic strain energy forces created in the lens during flexing of the haptics will aid, resist, or both aid and resist accommodation of the lens to its near vision position and return of the lens to its distant vision position depending upon the unstressed position of the lens.

During accommodation, the lens haptics 36 slide endwise in their fibrosed tissue pockets 42. As shown best in FIGS. 2 and 3, the haptics are tapered endwise in width and thickness to enable the haptics to move freely in the pockets. The lens optic 34 moves toward and away from the anterior capsular rim 22. The diameter of the optic is made as large as possible to maximize its optical imaging efficiency. The optic is preferably but not neccessarily made smaller than the diameter of the anterior capsule opening 26 to permit accommodation movement of the optic into and from the opening without interference by the capsular rim 22 in order to maximize the accommodation range. The actual lens dimensions are determined by each patient's ocular dimensions. The dimensions of a simple plate haptic intraocular lens according to the invention will generally fall within the following ranges:

Optic diameter: 3.0 mm–7.0 mm

Overall lens length: 9.0 mm–11.5 mm

Haptic thickness: 0.25 mm–0.35 mm

Refer now to FIGS. 9–15 illustrating several possible alternative shapes of the accommodating intraocular lens. The modified lens 50 illustrated in FIG. 9 is identical to lens 32 of FIGS. 1–8 except that the haptic hinges 38 of lens 32 are eliminated in the lens 50, and the haptics 52 of the lens 50 are flexible throughout their length, as illustrated by the broken lines in FIG. 9. The modified lens 54 in FIG. 10 has an anteriorly arched unstressed shape and includes a bi-convex optic 56, flexible hinges 58, and anteriorly vaulted haptics 60 with convex anterior surfaces 62. The convex anterior face 64 of the optic 56 and the convex anterior haptic surfaces 62 are rounded to a common radius. The modified intraocular lens 66 in FIG. 11 is relatively flat and includes an optic 68 having a planar Fresnel anterior face 70 and a convex posterior face 72, haptics 73, and flexible haptic hinges 74. The modified lens 76 in FIG. 12 has a posteriorly arched unstressed shape and includes an optic 78 having a planar anterior face 80 and a convex posterior face 82, haptics 84 having convex posterior surfaces 86 and haptic hinges 88. The posterior face 82 of the optic 78 and the posterior surfaces 86 of the haptics 84 are rounded to a common radius. The modified lens 90 illustrated in FIGS. 13 and 14 includes an optic 92 and flexible haptics 94 and has an unstressed near vision configuration shown in FIG. 13. The haptics flex to permit posterior deflection of the lens to its distant vision configuration of FIG. 14. The optic 92 is posteriorly offset relative to the inner ends of the haptics to permit greater anterior displacement of the optic during accommodation without contacting the anterior capsular rim 22 of the capsular bag 20. The modified intraocular lens 100 of FIG. 15 includes haptics 102 and an optic 104 which is offset anteriorly relative to the inner ends of the haptics. The haptics are joined to diametrically opposite sides of the optic by flexible hinges 106.

The modified intraocular lenses of FIGS. 9–15 are implanted within the capsular bag 20 of the eye 10 and utilize the posterior bias of the fibrosed capsular rim 22, the posterior capsule 24, changes in vitreous cavity pressure, and the patient's ciliary muscle action to effect accommodation in the same manner as described in connection with the intraocular lens 32 of FIGS. 1–8. In the case of the lens 100 in FIG. 15, the outer ends of its haptics 102 are implanted within the capsular bag 20 in essentially the same way as the haptics of lens 32 so that fibrosis of the rim 22 occurs about the haptics in the same manner as described in connection with FIGS. 1–8. The anteriorly offset optic 104 of the lens 100, on the other hand, protrudes through the anterior opening 26 in the capsular bag 20 and is situated anteriorly of the rim and between the rim and the iris 18 of the eye. There is sufficient space between the rim and the iris to accommodate the optic of a properly sized lens without the optic contacting the iris.

FIGS. 16–20 illustrate modified accommodating intraocular lenses according to the invention having means for fixating or anchoring the lens haptics in the capsular bag 20 to prevent the lenses from entering the vitreous cavity 21 of the eye in the event that the posterior capsule 24 becomes torn or a posterior capsulotomy must be performed on the posterior capsule because it becomes hazy. Except as noted below, the modified intraocular lenses of FIGS. 16–20 are identical to the lens 32 of FIGS. 1–8 and are implanted in the capsular bag 20 of the eye 10 in the same manner as described in connection with FIGS. 1–8. The intraocular lens 110 of FIGS. 16 and 17 is identical to lens 32 except that the outer ends of the lens haptics 112 have raised shoulders 114. Fibrosis of the capsular rim 22 around the haptics 112 and their shoulders 114 anchors or fixates the lens 110 in the capsular bag 20. The intraocular lens 116 of FIG. 18 is identical to lens 32 except that flexible stalk-like knobs 118 extend diagonally from the outer ends of the lens plate haptics 120. The distance between the outer ends of the diametrically opposed knobs 118 is slightly larger than the distance between the outer ends of the lens haptics and slightly larger than the diameter of the capsular bag 20. The knobs are set wider than the width of the lens body. These two features help to center the intraocular lens within the capsular bag so that the lens optic is centered immediately behind the circular capsulotomy 26 in the bag. Fibrosis of the capsular rim 22 around the haptics 120 and their knobs 118 fixes the lens 116 in the capsular bag 20. The intraocular lens 122 of FIG. 19 is identical to lens 32 except that the outer ends of the lens haptics 124 have openings 126. Fibrosis of the capsular rim 22 occurs around the haptics 124 and through their openings 126 to fixate the lens 122 in the capsular bag 20. The intraocular lens 128 of FIG. 20 is similar to the lens 122 in that the lens 128 has openings 130 in the outer ends of its haptics 132 through which fibrosis of the capsular rim 22 occurs to fixate the lens in the capsular bag 20. Unlike the lens 122, however, the haptic openings 130 are bounded along the outer ends of the haptics by spring loops 134. The overall length of the lens 128, measured between the centers of the spring loops 134 is made slightly greater than the maximum diameter of the capsular bag. The spring loops 134 press against and are deformed inwardly slightly by the outer circumference of the capsular bag to center the lens in the eye during fibrosis.

The modified intraocular lens 140 of FIG. 21 is identical to the lens 32 of FIGS. 1–8 except that the lens 140 has centration nipples 142 projecting endwise from the outer ends of the lens haptics 144 to compensate for slight differences, from one patient to another, in the diameter of the human capsular bag 20. Thus, the diameter of the capsular bag varies from about 11 mm in high myopes to about 9.5 mm in high hyperopes. The centration nipples 142 prevent differences in the degree of flexing of the haptics 144 in capsular bags of different diameters. For example, in a hyperopic eye with a small capsular bag, the lens haptics would flex more with marked posterior vaulting of the lens by the fibrosed capsular rim compared to the minimal vaulting of the haptics which would occur in high myopes with relatively large capsular bags. The nipples indent themselves into the outer circumference of the capsular bag to compensate for such differing bag diameters and thereby center the lens in the bag.

The modified intraocular lens 150 illustrated in FIGS. 22–24 comprises a lens body 152 proper identical to that of FIGS. 1–8 and springs 154 in the form of U-shaped hoops constructed of biologically inert spring material. The ends of these springs are fixed to the anterior sides of the lens haptics 156 adjacent the haptic hinges 158 in such a way that the arched ends of the springs extend a small distance beyond the outer ends of the haptics. The springs are stressed to normally lie relatively close to the anterior sides of the haptics. The lens body 152 is implanted within the capsular bag 20 of the eye 10 in the same way as described in connection with the lens 32 of FIGS. 1–8, and with the outer arched ends of the lens springs 154 lodged within the sulcus 19 of the eye between the iris 18 and the cornea 12. When the lens is in the position of FIG. 23 which it occupies immediately after surgery as well as after some degree of accommodation, the springs 154 lie relatively close to the anterior sides of the lens haptics 156. During posterior displacement of the lens to its distant vision position of FIG. 24 by the posterior bias of the fibrosed capsular rim 22, the springs are deflected anteriorly away from the lens haptics, as shown, thereby creating in the springs elastic strain energy forces which aid the stretched posterior capsule 24 and vitreous cavity pressure in displacing the lens anteriorly during accommodation in response to contraction of the ciliary muscle 28.

FIGS. 25–32 illustrate modified intraocular lenses according to the invention having a lens body and separate lens fixation elements for positioning the lenses in the capsular bag 20. Fibrosis of the capsular rim 22 occurs around these fixation elements in a manner which securely fixes the elements within the bag. In some figures, the lens body is separable from the fixation elements to permit removal of the lens from and replacement of the lens in its original position in the eye. In other figures, the lens body and fixation elements are secured against separation to prevent entrance of the lens body into the vitreous chamber in the event a tear develops in the posterior capsule 24 of the bag or a posterior capsulotomy is performed in the capsule.

The modified lens 160 of FIG. 25 includes a lens body 162 which is identical, except as noted below, to that of lens 32 in FIGS. 1–8 and separate fixation elements 164 at the outer ends of the lens haptics 166. The fixation elements and haptics are interengaged in such a way that the elements and haptics are capable of relative movement lengthwise of the haptics when the haptics flex during accommodation of the lens. The fixation elements 164 in FIG. 25 are generally U-shaped loops of biologically inert material having legs 168 which slide within longitudinal sockets 170 entering the outer ends of the haptics 166. The haptics 166 are somewhat shorter in length than those of the lens 32, and the overall length of the lens, measured between the outer arched ends of the fixation loops 164, when their legs 168 abut the bottoms of their sockets 170, is less than the maximum diameter of the capsular bag 20 when the ciliary muscle 28 is relaxed and greater than the diameter of the bag when the ciliary muscle is fully contracted for accommodation. The lens 160 is implanted within the capsular bag 20 of the eye 10 with the fixation loops 164 and the outer ends of the haptics 166 disposed between the anterior rim 22 and posterior capsule 24 of the capsular bag 20. The outer arched ends of the loops are situated at the outer circumference of the bag.

Fibrosis of the capsular rim 22 occurs around the outer ends of the lens haptics 166 and the exposed outer ends of the fixation loops 164 and through the spaces between the haptics and the loops in such a way that the loops are firmly fixed in the capsular bag, and the haptics form pockets 42 in the fibrose tissue F. The posterior bias of the fibrosed capsular rim 22 urges the lens posteriorly to its distant vision position when the ciliary muscle 28 is relaxed, thereby stretching the posterior capsule 24 rearwardly in the same manner as explained in connection with FIGS. 1–8. When the ciliary muscle contracts during accommodation, the vitreous cavity pressure increases and the capsular rim 22 relaxes, thereby permitting the stretched posterior capsule and the vitreous cavity pressure to push the lens body 162 forwardly toward its near vision position, again in the same manner as explained in connection with FIGS. 1–8. Contraction of the capsular bag in response to contraction of the ciliary muscle during accommodation displacement exerts inward forces on the fixation loops 164. These inward forces urge the loops inwardly in their haptic sockets 170 until the loops abut the bottoms of the sockets. The inward forces exerted on the loops then produce an anterior buckling moment on the lens body 162 which aids accommodation of the lens by the posterior capsule. During this accommodation, the lens haptics 166 flex posteriorly relative to the lens optic 172 and slide inwardly in their fibrose pockets 42 and along the legs 168 of the fixation loops 164, the movement being aided by hinges 38.

The fixation loops have holes 174 in their outer arched ends through which a suture 176 may be passed and tied to retain the loops and lens body in assembled relation during implantation of the lens in the capsular bag. This suture is removed at the conclusion of the surgery. Holes 174 may also be utilized to position the lens in the capsular bag during surgery. The lens haptics 166 are separable from and reengageable with the fixation loops 164. This permits the lens body 162 to be removed from the eye any time after surgery for correction or replacement of the lens optic 172 and then replaced in its original position in the eye.

The modified intraocular lens 180 of FIG. 26 is similar to that of FIG. 25 except for the following differences. First, the haptics 182 of lens 180 are substantially the same length as the haptics of lens 32 and have cutouts 184 in their outer ends. The legs 188 of the fixation loops 186 slide in sockets 190 which enter the bottom edges of the cutouts 184. When the lens is implanted within the capsular bag 20, the tongue-like haptic portions at opposite sides of the haptic cutouts 184 and the outer arched ends of the fixation loops 186 are situated within the outer circumference of the bag. As with the lens of FIG. 25, fibrosis of the capsular rim 22 occurs around the haptics 182 and fixation loops 186 and through the spaces between the haptics and loops so as to firmly fix the loops in the capsular bag and form pockets within which the haptics slide when they flex during accommodation of the lens. Secondly, the legs 188 of the fixation loops 186 and their sockets 190 in the lens haptics 182 are tapered to facilitate free relative movement of the loops and haptics when the haptics flex during accommodation. Thirdly, the fixation loops have fixation nipples 192 at their outer arched ends which indent into the outer circumference of the capsular bag 20 to retain the lens against movement relative to the bag during fibrosis.

FIG. 27 illustrates a modified intraocular lens 196 like the lens 180 illustrated in FIG. 26 except that the legs 198 of the fixation loops 200 and the haptic sockets 202 which receive these legs have coacting shoulders 204, 206. These shoulders permit limited relative movement of the lens body 208 and loops when the haptics 210 flex during lens accommodation, but secure the lens body and loops against complete separation so as to prevent the lens body from entering the vitreous chamber 21 if a tear occurs or a capsulotomy is performed in the posterior capsule 24. Another difference between the lens 196 and the lens 180 resides in the fact that the hinges 212 connecting the inner ends of the haptics 210 to the lens optic 214 extend across only an intermediate portion of the haptic width. The remaining lateral portions of the inner haptic ends beyond the ends of the hinges are separated from the optic by arcuate slots 216 centered on the axis of the optic. These separations of the haptics from the optic permit the optic to move freely into and from the anterior opening 26 in the capsular bag 20 without interference with the capsular rim 22 during lens accommodation. The generally triangular haptic portions adjacent the slots 216 prevent the rim 22 of the capsular bag 20 from fibrosing between the lens optic 214 and the inner ends of the lens haptics 210 and thereby restricting endwise movement of the haptics in their fibrosed pockets 42.

Figure 28:
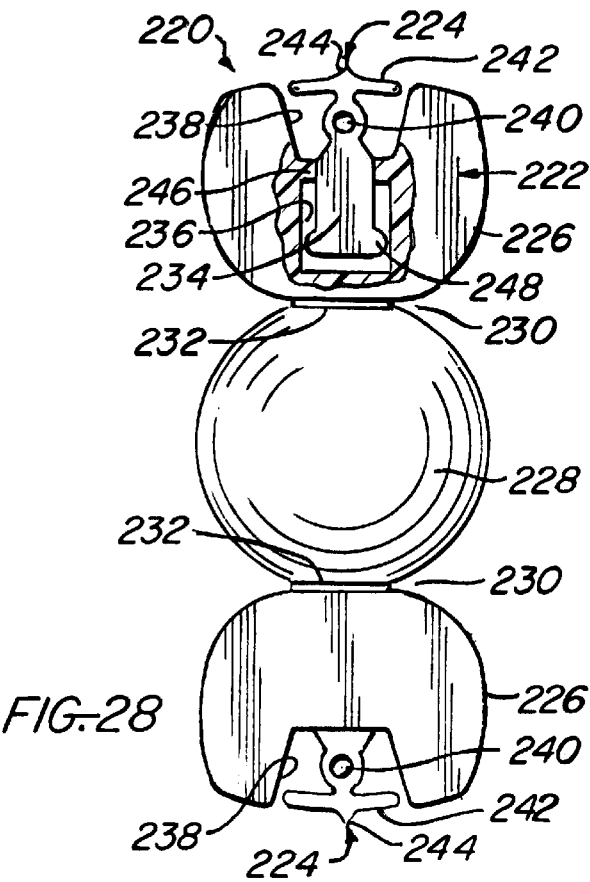

The modified lens 220 of FIG. 28 includes a lens body 222 and separate fixation elements 224 at the outer ends of the lens haptics 226. The inner ends of the haptics are convexly curved and disposed in generally tangential relation to diametrically opposite sides of the lens optic 228 so as to provide relatively large clearance spaces 230 between the optic and the inner haptic ends. The haptics and optic are joined along their tangential portions by flexible hinges 232. The fixation elements 224 are generally cruciform shaped pins having inner journals 234 which slide within bearing bores 236 entering the bottom edges of cutouts 238 in the outer ends of the haptics 226. These fixation pins have holes 240 between their ends, outer cross arms 242, and nipples 244 at their outer ends. The length of the lens 220 measured between the outer ends of its haptics 226 and fixation pins 224 approximates the maximum inner diameter of the capsular bag 20 when the ciliary muscle is relaxed. The fixation pin journals 234 and their bores 236 have coacting shoulders 246, 248 which permit limited relative movement of the lens body and fixation pins when the haptics flex during accommodation but secure the body and fixation pins against complete separation, for the same reasons as explained above in connection with FIG. 27. If desired, the shoulders 246, 248 may be eliminated to permit separation of the fixation pins and lens body for the same reasons as explained in connection with FIG. 26. If the shoulders are eliminated, a removable suture may be threaded through the fixation pin holes 240 and tied to hold the fixation pins and lens body in assembled relation during implantation of the lens, as explained in connection with FIG. 25. The holes may also be used to position the lens in the capsular bag during implantation of the lens.

When the lens 220 is implanted within the capsular bag 20 of the eye 10, the outer ends of the lens haptics 226 and the fixation pins 224 are disposed between the capsular rim 22 and posterior capsule 24 of the bag in much the same way as described in connection with FIGS. 25–27. The nipples 244 indent the outer circumference of the bag to fix the lens against rotation circumferentially around the bag and center the lens in the eye during fibrosis of the rim 22. Fibrosis of the capsular rim occurs about the outer ends of the haptics and the fixation pins to firmly fix the pins in the bag and form pockets in the fibrosed tissue receiving the haptics. The lens body 222 is urged posteriorly to its distant vision position by the posterior bias of the capsular rim 22 when the ciliary muscle 28 relaxes and anteriorly toward its near vision position during accommodation by the stretched posterior capsule 24 and increase in vitreous cavity pressure when the ciliary muscle contracts, all in essentially the same way as explained earlier in connection with FIGS. 25–27. During anterior accommodation of the lens, contraction of the capsular bag 20 in response to contraction of the ciliary muscle exerts inward forces on the outer ends of the haptics 226 which produce an anterior buckling moment on the lens body 222 that aids lens accommodation by the posterior capsule. The cross arms 242 of the fixation pins 224 are enveloped by the fibrosed tissue F during fibrosis of the rim 22 to provide pivots about which the pins can rotate during buckling of the lens body in the course of lens accommodation. The spaces 230 between the inner ends of the haptics 226 and the optic 228 accommodate movement of the optic into and from the opening 26 in the capsular bag without interference with the surrounding capsular rim 22.

Figure 29:
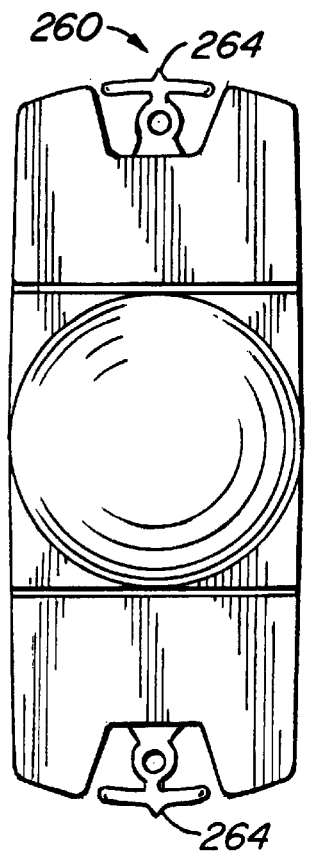
Figure 30:
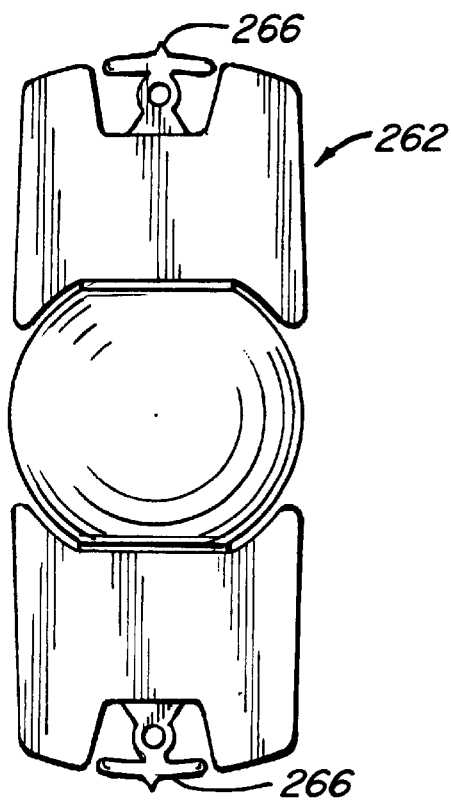

The modified intraocular lenses 260, 262 in FIGS. 29 and 30 are identical to the lenses 180, 196, respectively, in FIGS. 26 and 27 except that the fixation loops of the latter lenses are replaced, in FIGS. 29 and 30, by fixation pins 264, 266 like those in FIG. 28.

Figure 31:
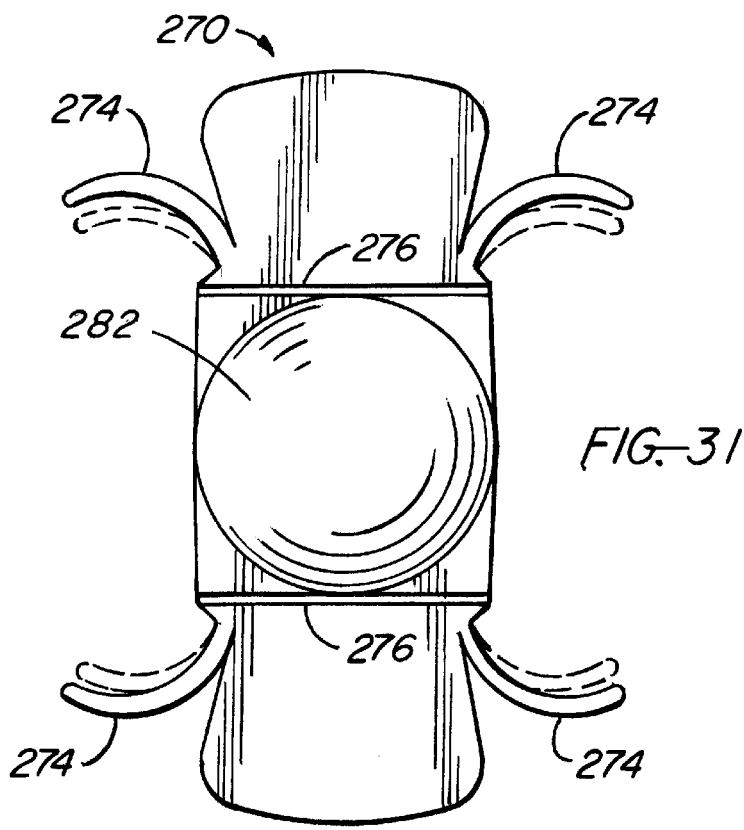
FIGS. 31–34 illustrate modified accommodating intraocular lenses according to the invention having integral fixation means.
Figure 32:
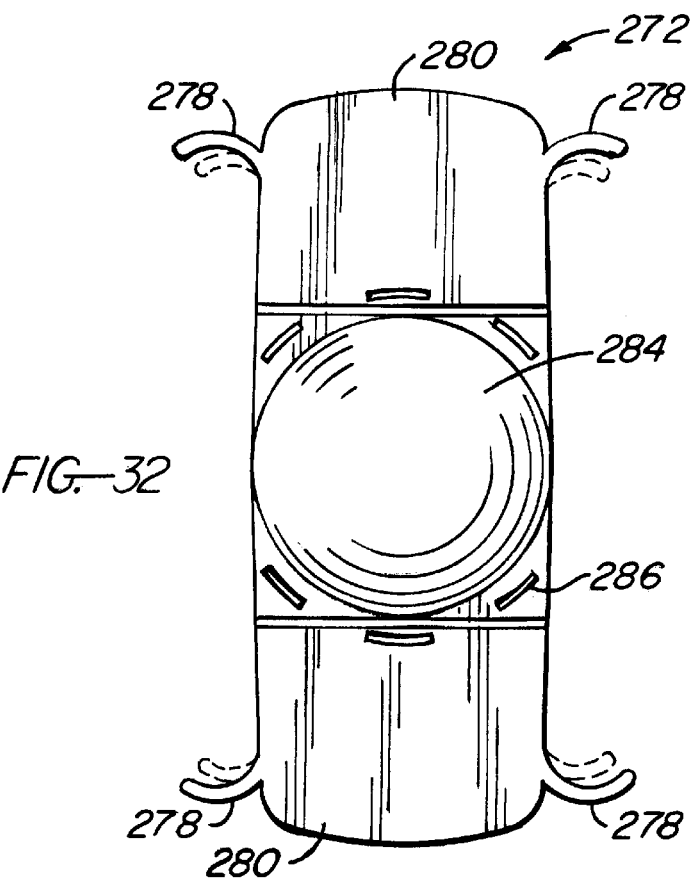

The modified intraocular lenses 270, 272 in FIGS. 31 and 32 are identical to the lens 32 of FIGS. 1–8 except that lens 270 has lateral spring arms 274 which extend from the haptic hinges 276 and lens 272 has lateral spring arms 278 which extend from the edges of the lens haptics 280. The arms 274, 278 extend laterally from and longitudinally toward the outer ends of the lens haptics in such a way that in their normal unstressed Positions, the arms are disposed at acute angles relative to the longitudinal axes of the lenses. The arms are sized in length so that when the lenses are implanted within the capsular bag 20 of the eye, the outer ends of the arms press against the outer circumference of the bag and are thereby curled or compressed to the positions illustrated in broken lines. The curl or compression in the arms decreases when the capsular bag expands in response to relaxation of the ciliary muscle during distant vision accommodation of the lens and increases when bag contracts in response to contraction of the ciliary muscle during near vision accommodation of the lens. Engagement of the arms with the capsular bag circumference acts to center the lenses in the bag in a position wherein the lens optics 282, 284 are coaxially aligned with the anterior bag opening 26. Fibrosis of the capsular rim 22 occurs about the spring arms to fix the lenses within the capsular bag and about the lens haptics to form pockets in which the haptics slide when they flex during accommodation of the lenses.

Referring to FIG. 32 and to FIGS. 4 to 8, projections such as those indicated at 286 in FIG. 32, may preferably be provided in various embodiments of the invention to space the capsulorhexis from the optic when the capsulorhexis constricts from its configuration shown in FIGS. 5 to 8. This spacing prevents the anterior capsular rim 22, with a relatively small capsular opening 26, from encroaching onto the optic during fibrosis of capsular rim 22. As shown in FIG. 32, such projections 286 extend outwardly anteriorly from the plate haptic surface, and are disposed about and spaced from the optic. The projections extend outwardly no farther than the outer extent of the optic, typically to a height of about 1–1.5 mm. The projections may be in the form of continuous arcs (not shown) and may be inclined outwardly relative to the optic.

Figure 33:
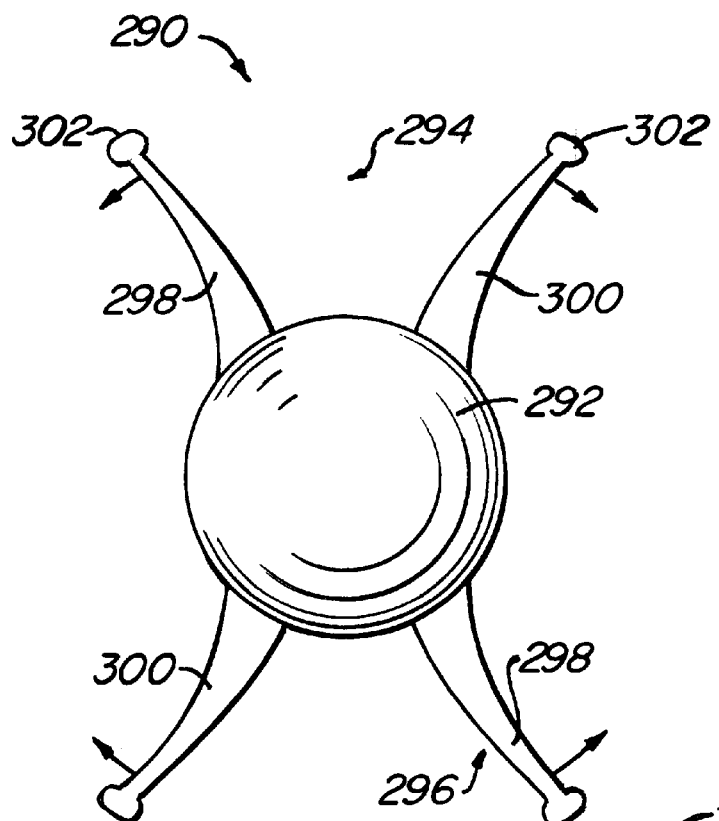

The modified accommodating intraocular lens 290 of FIG. 33 comprises a circular optic 292 and two pairs 294, 296 of curved, flexible haptics 298, 300 extending from opposite edges of the optic. These haptics have the form of relatively slender arms. At the outer ends of the haptics are enlarged knobs 302. The two haptics 298 of each haptic pair 294, 296 extend out from the optic 292 in mutually divergent relation and curve away from one another toward their outer ends, as shown. The four haptics are disposed in symmetrical relation relative to a plane of symmetry containing the axis of the optic and passing midway between the two haptics of each haptic pair. The two haptics 298 are located diametrically opposite one another, and the two haptics 300 are located diametrically opposite one another. The diametrical distance measured between the outer ends of the diametrically opposed haptics 298, 300 is made slightly greater than the maximum diameter of capsular bag 20. The lens 290 is implanted within the bag in much the same manner as the earlier embodiments of the invention and with the outer ends of the lens haptics 298, 300 disposed between the anterior capsular rim 22 and posterior capsule 24 of the bag. The outer ends of the haptics press resiliently against the outer circumference of the bag and flex or bend in such a way as to both accommodate bags of different diameter and center the optic 292 behind the anterior capsulotomy in the bag. The anterior capsular rim 22 of the bag fibroses about the haptics to fixate the lens in the bag. After fibrosis is complete, brain initiated relaxation and constriction of the ciliary muscle 28 of the eye is effective to cause accommodation of the lens between near and distant vision positions in essentially the same manner as described earlier. During this accommodation, the lens buckles and the haptics flex anteriorly and posteriorly relative to the optic 292 in much the same way as described earlier. Fibrosis of the capsular rim about the haptic knobs 302 fixates the lens in the capsular bag and against dislocation in the event a tear or capsulotomy is formed in the posterior capsule 24 of the bag.

Figure 34:
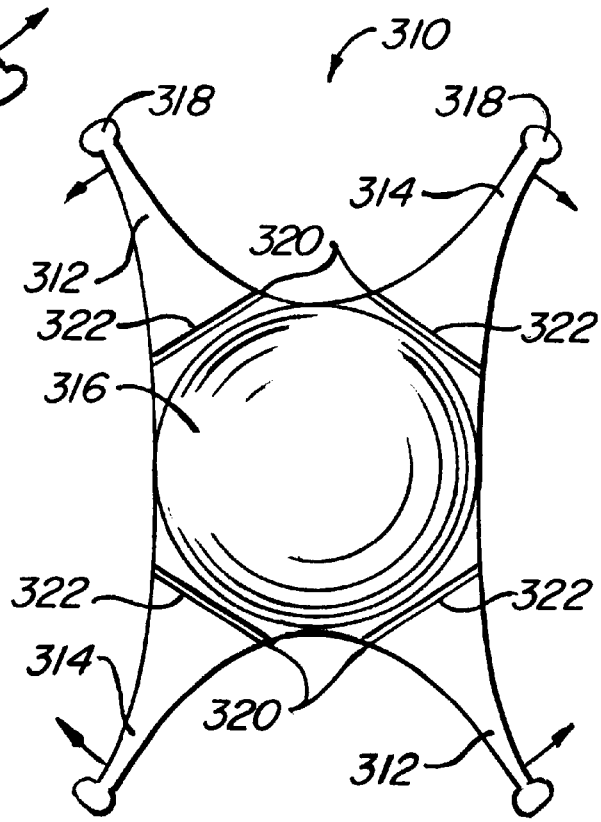

The modified accommodating intraocular lens 310 of FIG. 34 is similar to the lens 290 of FIG. 33 and differs from the lens 290 only in the following respects. The four haptics 312, 314 of the lens 310, rather than being slender curved arms like those of lens 290, are symmetrically tapered from relatively wide inner ends which are joined to the lens optic 316 to relatively narrow outer ends. At the outer ends of the haptics 312, 314 are enlarged knobs 318. At inner ends of the haptics are grooves 320 which form flexible hinges 322 about which the haptics are flexible anteriorly and posteriorly of the optic. The diametrical distance between the outer ends of the diametrically opposed haptics 312, 314 approximates or slightly exceeds the maximum diameter of the capsular bag 20. The lens 310 is implanted within the bag, and fibrosis of the anterior capsular rim 22 of the bag occurs about the lens haptics in the same way as described in connection with lens 290. After fibrosis is complete, brain initiated relaxation and constriction of the ciliary muscle 28 of the eye cause accommodation of the lens in the same manner as described in connection with lens 290. Fibrosis of the capsular rim about the haptic knobs 318 fixates the lens in the capsular bag and against dislocation in the event a tear or capsulotomy is formed in the posterior capsule 24 of the bag.

The accommodating plate haptic lenses described to to this point are referred to herein as simple plate haptic lenses.

These lenses are intended for use when the anterior capsulotomy procedure performed on the eye provides an anterior annular capsular remnant or rim that remains intact and circumferentially continuous throughout fibrosis and has a sufficient radial width to retain the lens in the proper position within the capsular bag during and/or after fibrosis. According to another of its aspects, this invention provides modified accommodating intraocular lenses, illustrated in FIGS. 38–40 and 43–46 and referred to as plate haptic spring lenses, for use when the anterior capsular remnant or rim of the capsular bag is ruptured, that is cut or torn, or has too small a radial width to firmly retain the lens in proper position during and/or after fibrosis.

As noted earlier, a ruptured capsular remnant or rim may occur in different ways. For example, continous tear circular capsulotomy, or capsulorhexis, (FIG. 35) involves tearing the anterior capsule of the natural lens along a circular tear line to form in the anterior capsule a circular opening or capsulotomy 400 circumferentially surrounded by an annular remnant or rim 402 of the anterior capsule. Improper performance of this capsulorhexis can easily create slits or tears 404 in the capsular rim. A beer can or can opener capsulotomy (FIG. 36) involves piercing the anterior capsule of the natural lens at a multiplicity of close positions 404 along a circular line and removing the circular portion of the anterior capsular rim within the pierced line to form an anterior capsule opening 406 circumferentially surrounded by an annular rim 408. While this rim may be initially intact and circumferentially continuous, it has an inner scalloped edge 410 having stress-inducing regions that render the rim very prone to tearing radially, as shown at 411, during surgery or subsequent fibrosis. An envelope capsulotomy (FIG. 37) involves slitting the anterior capsule of the natural lens along a horizontal line 412, then along vertical lines 414 extending upwardly from and intersecting the horizontal slit, and then tearing the anterior capsule along a tear line 416 which arches upwardly from the upper end of the vertical slit and then extends vertically downward to join the second vertical cut. This capsulorhexis produces an anterior capsule opening 418 bounded by a capsular remnant 420 which is slit at 412 and hence is inherently ruptured.

A ruptured anterior capsular remnant or rim may preclude utilization of a simple plate haptic lens of the invention for the following reasons. A ruptured rim may not firmly retain the lens haptics in the sulcus of the capsular bag during fibrosis. This renders the lens prone to decentration and/or dislocation, such as dislocation into the vitreous cavity if the posterior capsule tears or becomes cloudy over a period of time and is cut with a laser to provide a capsulotomy in the posterior capsule. A ruptured capsular rim may be incapable of assuming the taut trampoline-like condition of an intact capsular rim. As a consequence, a ruptured capsular rim may be incapable of effecting full posterior deflection of a plate haptic lens to a distant viewing position against the posterior capsule during and after fibrosis. A ruptured capsular rim may also permit anterior deflection of the lens during fibrosis. In either case, since the power of an intraocular lens is selected for each individual patient and may be dependent upon their spectacle power, and since good vision without glasses requires the lens optic to be situated at precisely the correct distance from the retina throughout the range of accommodation, a simple plate haptic lens of the invention may not be acceptable for use with a ruptured anterior capsular remnant or rim.

Figure 35:
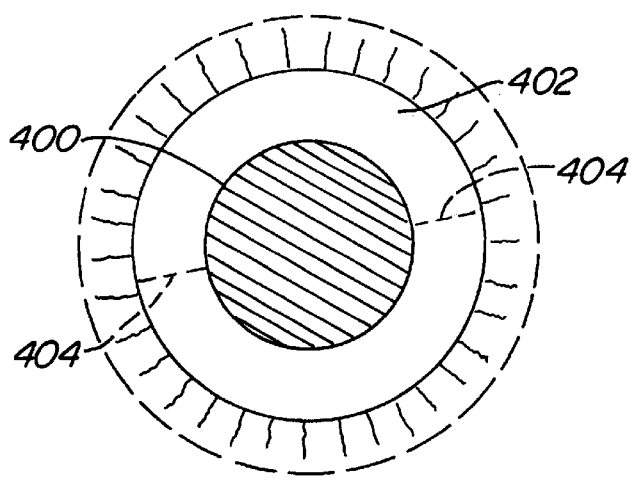
FIGS. 35–37 illustrate the capsulotomy produced by a continuous tear circular capsulotomy (capsulorhexis), a beer can capsulotomy, and an envelope capsulotomy, respectively.
Figure 36:
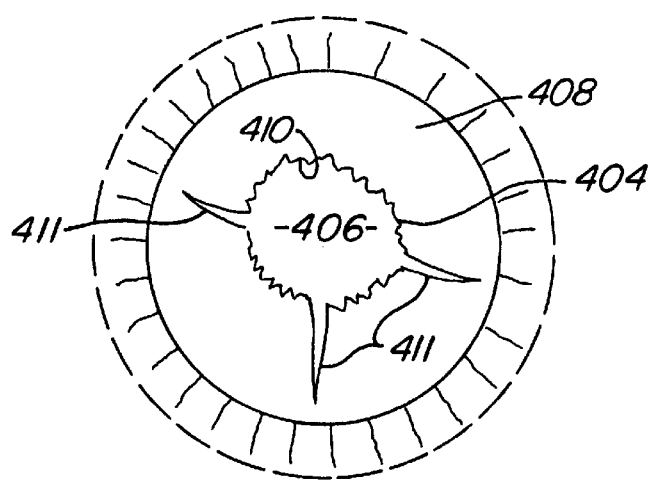
Figure 37:
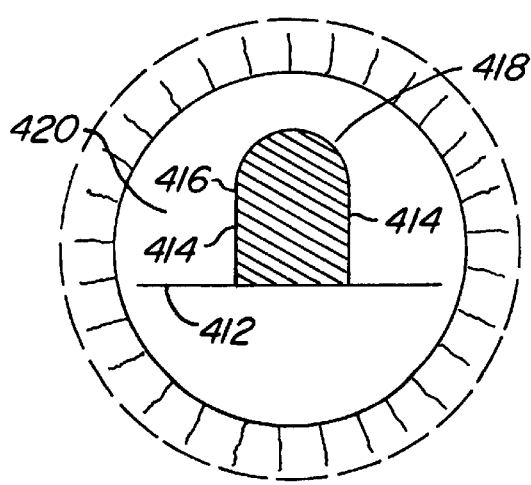
Figure 38:
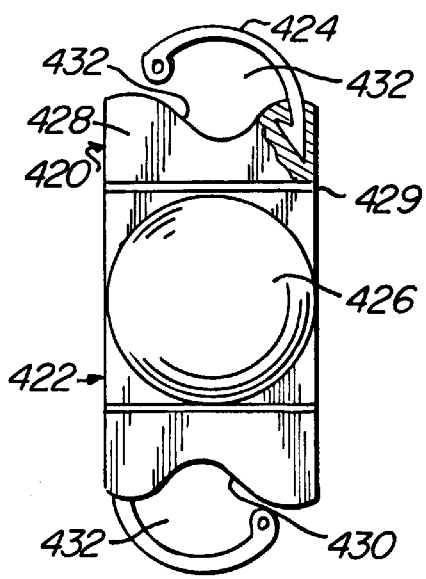
FIG. 38 is an anterior face view of a plate haptic spring lens according to the invention.
Figure 39:
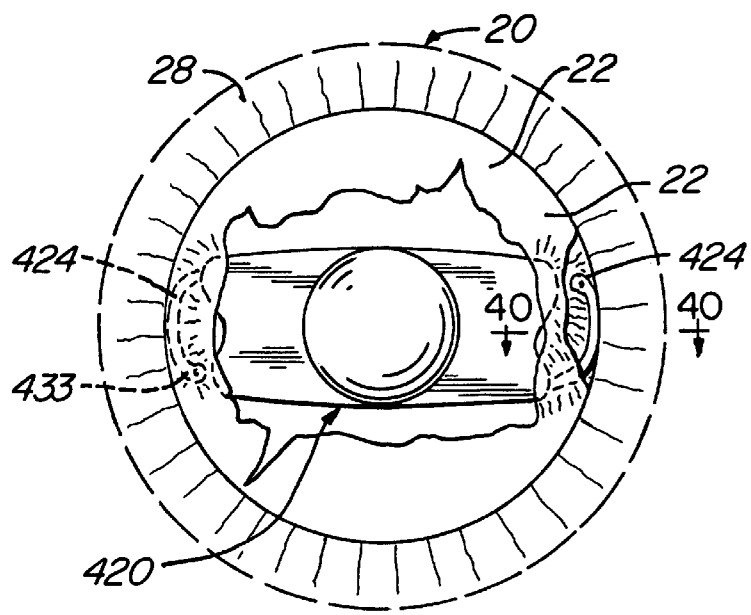
FIG. 39 is a view similar to FIG. 4 showing the plate haptic spring lens of FIG. 38 implanted within the eye.
Figure 40:
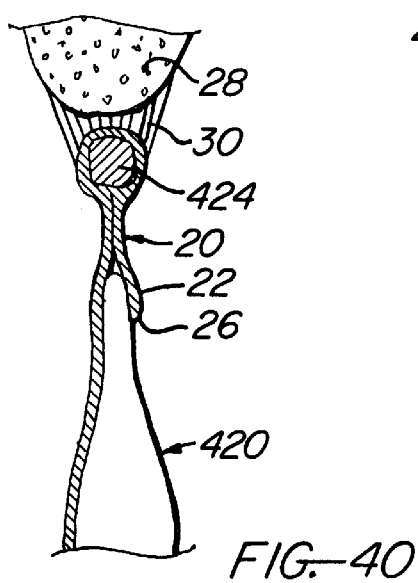
FIG. 40 is an enlarged section taken on line 40—40 in FIG. 39.

FIGS. 38–40 illustrate an accommodating plate haptic spring intraocular lens 420 of the invention for use with a ruptured anterior capsular remnant or rim, such as any one of those illustrated in FIGS. 35–37. This plate haptic spring lens has a lens body 422 similar to that of the plate haptic lens 32 in FIGS. 1–8 and springs 424 at the ends of the body. The lens body 422 includes a central optic 426 and flexible plate haptics 428 extending outward from diametrically opposite sides of the optic. These haptics are joined to the optic by hinges 429 formed by grooves in the anterior side of the lens. The springs 424 are resilient loops which are staked at one end to the ends of the haptics 428 at opposite sides of the longitudinal centerline of the body. These spring loops bow outwardly lengthwise of the lens body from their staked ends to their centers and then turn back toward the lens body from their centers to their free ends. The ends of the haptics 428 have recesses 430 over which the spring loops extend in such a way that the loops and the edges of the recesses form openings 432 therebetween. The ends of the spring loops have holes 433 to receive instruments for positioning the lens in the eye.

The plate haptic spring lens 420 is implanted within the capsular bag 20 of the eye in the same manner as described earlier in connection with the simple plate haptic lenses of the invention. That is to say, the lens 420 is implanted within the eye while its ciliary muscle 28 is paralyzed in its relaxed state, and the capsular bag is thereby stretched to its maximum diameter (9–11 mm). The overall length of the lens body 422 measured between the ends of the lens haptics 428 at either side of the haptic recesses 430 substantially equals the inner diameter of the stretched capsular bag. The overall length of the lens measured between the outer edges of the spring loops 424 at their centers when the loops are in their normal unstressed state is slightly greater than this inner diameter of the stretched capsular bag. For example, if the inner diameter of the stretched capsular bag is in the range 10–10.6 mm, the lens body 422 will have an overall length of 10–10.6 mm measured between the outer ends of the lens haptics, and the overall length of the lens measured between the centers of the unstressed spring loops will be in the range of 11–12.5 mm.

FIGS. 39 and 40 illustrate the plate haptic spring lens 420 implanted in a capsular bag 20 which is stretched by relaxation of the ciliary muscle 28 and has a torn anterior capsular rim 22 such as might result from an improperly performed continuous tear circular capsulorhexis. Because the rim is torn, the lens body 422 will not fit as snugly in the stretched bag as it would if the capsular rim were an intact rim free of tears. The haptic spring loops 424, however, press outward against the wall of the capsular bag sulcus about the rim of the bag to fixate the lens in the bag during fibrosis following surgery. Fibrosis of the torn capsular rim 22 occurs about the outer ends of the plate haptics 428, about the spring loops 424, and through the openings 432 between the loops and the ends of the haptics in such a way as to effect fusion of the torn rim, or more precisely the remnants of the torn rim, to the posterior capsule 24 of the capsular bag. The outer ends of the haptics and the spring loops are thereby shrink-wrapped by fibrosis in somewhat the same manner as explained earlier in connection with the simple plate haptic lenses of the invention. Even though the torn capsular rim 22 may be incapable of stretching to the taut trampoline conditon discussed earlier when the ciliary muscle is relaxed, this shrink-wrapping of the lens during fibrosis of the torn rim will firmly fixate the lens in the capsular bag and should cause some posterior deflection of the lens against the elastic posterior capsule 24. Accordingly, brain-induced constriction and relaxation of the ciliary muscle 28 after fibrosis of the torn capsular rim is complete should effect accommodation of the plate haptic spring lens in much the same way, but possibly not with the same amount of accommodation, as the simple plate haptic lens with an intact non-ruptured capsular rim.

While the plate haptic spring lens 420 is designed for use with a ruptured anterior capsular remnant or rim, it can also be utilized with an intact rim. A plate haptic spring lens also compensates for improper lens placement in the eye with one end of the lens situated in the capsular bag and the other end of the lens situated in the ciliary sulcus of the eye since the spring loops will expand outwardly to engage both the inner edge of the bag and the wall of the ciliary sulcus. In this regard, an advantage of the plate haptic spring lenses of the invention over the simple plate haptic lenses resides in the fact that the spring lenses eliminate the need to have on hand in the operating room both a simple plate haptic lens for use with an intact capsular rim and a plate haptic spring lens as a backup for the plate haptic lens in the event the rim is ruptured during surgery.

Another advantage of the haptic spring lens 420 resides in the fact that it permits the lens to have a larger optic than a simple plate haptic lens whose optic diameters will normally be within the range of 4–7 mm. Thus, since the haptic spring lens relies on the spring loops 424 rather than on the capsular remnant or rim 22 to retain the lens in position during fibrosis, the lens may be used with a capsular remnant or rim of smaller radial width and hence larger diameter anterior capsule opening than those required for use of the simple plate haptic accommodating lenses. The larger diameter anterior capsule opening, of course, permits a larger optic diameter in the range of 7–9 mm which offers certain ophthalmological benefits.

Figure 41:
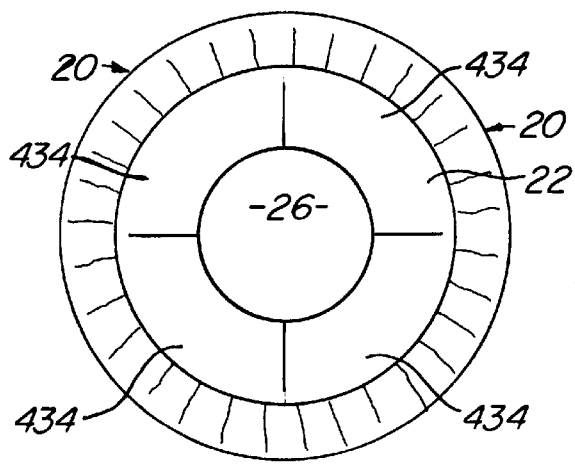
FIGS. 41 and 42 illustrate two ways of enlarging the capsulotomy of a capsular bag after completion of fibrosis to allow anterior movement of a relatively large lens optic.
Figure 42:
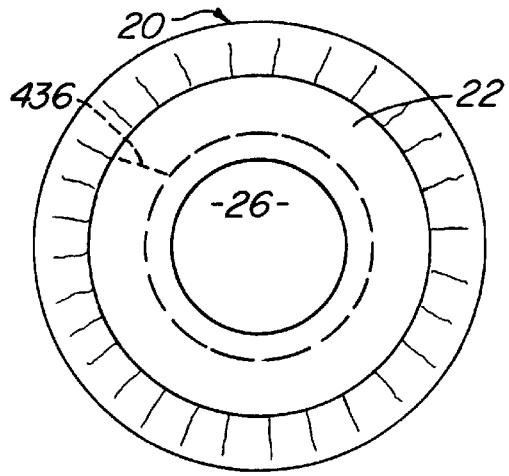

The large diameter anterior capsule opening necessary to accommodate a large optic spring accommodating lens may be formed during the original surgery by a planned large continuous tear circular capsulorhexis, a beer can capsulotomy of the desired large diameter, a planned envelope capsulotomy or by cutting of radial slits into the anterior capsular rim during surgery after implanting the spring accommodating lens in the capsular bag. According to another of its aspects, the invention provides a method whereby the desired large anterior capsule opening may be formed after the original surgery following completion of fibrosis. This method involves slitting an annular capsular rim radially with a laser after fibrosis is complete into a number of flap-like remnants 434 (FIG. 41) which are easily displaced by the lens during accommodation to permit the lens optic to pass through the anterior capsule opening. Alternatively, the anterior capsule opening may be enlarged by cutting the capsular rim with a laser circumferentially along a circular line 436 (FIG. 42) concentric with and radially outwardly of the original edge of the opening to enlarge the latter.

Figure 43:
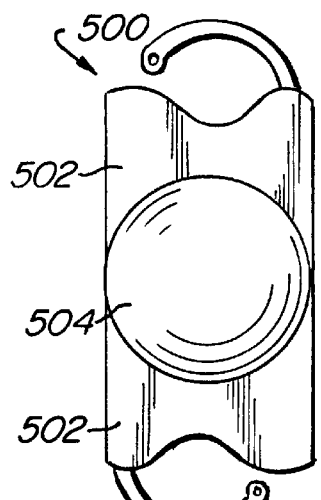
FIG. 43 is an anterior side view of a modified plate haptic lens according to the invention.
Figure 44:
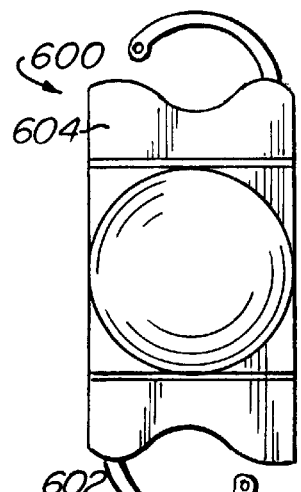
FIGS. 44–46 illustrate modified plate haptic spring lenses according to the invention.
Figure 45:
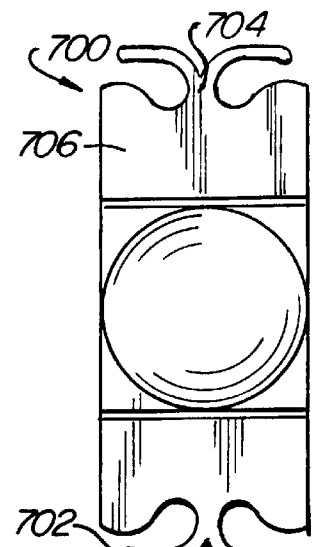
Figure 46:
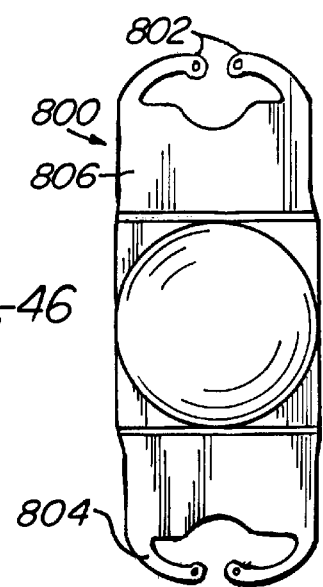

The modified plate haptic spring lens 500 of FIG. 43 is identical to the lens 420 just described except that the haptics 502 of the modified lens, rather than being hinged to the lens optic 504, are resiliently flexible throughout their length like those of the plate haptic lens in FIG. 9. FIG. 44 illustrates a further modified plate haptic spring lens 600 according to the invention which is identical to the lens 420 except that the spring loops 602 of the modified lens are formed integrally with the lens haptics 604. The modified lens 700 and 800 of FIGS. 45 and 46 are identical to the lens 600 except that the modified lenses have a pair of spring loops at each end. The spring loops 702 of lens 700 have common base portions 704 integrally joined to the ends of the lens haptics 706 along the longitudinal centerline of the lens and free ends which curve outwardly from the base portions both endwise and laterally of the lens. The spring loops 802 of lens 800 have base portions 804 integrally joined to the ends of the lens haptics 806 along the longitudinal edges of the haptics and opposite free ends which curve inwardly toward one another laterally of the lens.

FIGS. 47–50 illustrate the presently preferred accommodating intraocular lens of the invention. The illustrated lens 900 is a plate haptic spring lens having a body 902 including a round bi-convex optic 904 and plate haptics 906 joined to diametrically opposite sides of the optic by hinge junctions 908.

Haptics 906 have relatively wide outer end portions 910, inwardly tapered central portions 912, and relatively narrow tapered inner end portions 914. The inner end portions 914 are joined to diametrically opposite edge portions of the round optic 904. The width of the outer end portions 910 of the haptics measured transverse to the length of the lens approximates the diameter of the optic. The width of the inner haptic end portions 914 measured transverse to the length of the lens is substantially less than the diameter of the optic. The outer end portions 910 and tapered central portions 912 of the haptics occupy the major length of the haptics measured in the lengthwise direction of the lens. The tapered inner end portions 914 of the haptics taper inwardly to a progressively narrower width toward the outer ends of the haptics. These inner end portions effectively form bridges between the optic and the wide outer major portions 910 of the haptics. The inner haptic end portions contain V-grooves 916 which extend across the anterior sides of these end portions transverse to the length of the lens close to and preferably in virtually tangential relation to the edge of optic 904.

The outer end portions 910 of the haptics 906 contain relatively large openings 918 in the form of cutouts which open through the outer ends of the haptics. Joined at one end to the outer ends of the haptics, at one side of the open ends of the haptic cutouts 918, are spring arms 920. These arms extend laterally across the outer haptic ends and are resiliently flexible endwise of the lens.

As shown in FIG. 48, the optic 904 is offset anteriorly relative to the plate haptics 906. That is to say, a plane (median plane) containing the circumferential edge of the lens is offset anteriorly along the lens axis relative to a plane (median plane) passing through the haptics parallel to and midway between their anterior and posterior sides. This anterior offset of the optic provides groove-like recesses 924 at the posterior side of the lens along the junctures of the optic and the inner ends 914 of the haptics. The relatively thin web-like portions of the lens body between the anterior grooves 916 and posterior recesses 924 are resiliently flexible and form the hinge junctions 908 about which the lens haptics are flexible anteriorly and posteriorly relative to the lens optic.

Referring to FIG. 49, the lens 900 is implanted in the capsular bag 20 of a patient's eye, and following completion of fibrosis, undergoes accommodation in response to contraction and relaxation of the ciliary muscle 28 in much the same manner as described in connection with the earlier described lens embodiments of the invention. The spring arms 920 of the lens press outwardly against the outer perimeter of the bag to position the lens in the bag even though the anterior remnant 22 of the bag may be slit, torn, or otherwise not intact, in the same manner as described in connection with FIGS. 38–40. During fibrosis of the anterior capsular rim 22 of the bag 20 to the elastic posterior capsule 24 following surgery, fibrosis occurs around the lens haptics 906 and through the haptic openings 918 to fixate the lens in the capsular bag. The ciliary muscle 28 is maintained in its relaxed state until fibrosis is complete by introducing a cycloplegic into the eye, as explained earlier.

The anterior offset of the optic 904 in the preferred lens 900 provides two advantages. One of these advantages resides in the fact that the arrangement of the hinge junctions 908 resulting from the anterior offset of the optic 904 aids anterior buckling of the lens and thereby accommodation movement of the optic relative to the outer ends of the haptics 906 in response to endwise compression of the lens by contraction of the ciliary muscle 28. The other advantage resides in the fact that the hinge junctions 908 which join the haptics 906 to the diametrically opposite edge portions of the optic 904 are relatively narrow compared to the diameter of the optic and are preferably narrower than the radius of the bag, as shown. The hinge junctions thus occupy only relatively small circumferential edge portions of the optic. The remaining circumferential edge portions of the optic between the junctions are free edge portions which are totally unobstructed by the haptics and taken together constitute a major portion of the optic circumference. The diameter of the optic is made to approximate or be slightly smaller than the anterior capsule opening 26 in the capsular bag in which the lens is implanted. These features of the lens enable the lens to undergo increased anterior accommodation movement from its posterior distant vision position of FIG. 49 to its forward accommodation limit of FIG. 50, in which the optic projects through the anterior capsule opening 26, in response to contraction of the ciliary muscle 28. The inward taper of the inner bridge portions or ends 914 of the haptics permit these haptic portions to slide in and out of the capsular bag haptic pockets during accommodation of the lens.

The actual dimensions of the preferred lens may vary depending upon the patient's ocular dimensions. Following are typical lens dimensions:

Overall lens length: 10.5 mm
Overall lens length including springs: 11.5 mm
Optic diameter: 4.50 mm
Haptic outer end width: 4.50 mm
Haptic edge taper angle: 30 degrees
Length of inner haptic end portion: 0.75 mm
Haptic thickness: 0.25–0.4 mm
Hinge junction width: 1.50 mm
Lens material: silicone In the lens 900 of FIGS. 48–50, the optic 904 is offset anteriorly relative to the haptics 906 within the thickness of the haptics in such a way that both the circumferential edge of the optic and the hinge junctions 908 are situated within the thickness of the haptics and between their anterior and posterior surfaces. FIG. 51 is a longitudinal cross-section similar to FIG. 48 through a modified intraocular lens 900a of the invention which is identical to lens 900 except that the optic 904a of the lens 900a is offset anteriorly relative to the haptics 906a outside the thickness of the haptics. That is to say, in the lens 900a, both the circumferential edge of the optic 904a and the hinge junctions 908a between the optic and haptics are located forwardly of the anterior surfaces of the haptics 906a. This modified lens configuration provides the same advantages as that of FIGS. 48–50.

The modified accommodating intraocular lens 900b of FIG. 52 is essentially identical to the lens 900 except for the following differences. Integrally joined at their ends to and extending across the outer ends of the lens haptics 906b are relatively slender bridges or arches 922b which bound and close the adjacent sides or ends of the haptic openings 918b. These arches are typically 0.20 mm in width and curved to a radius of 5.25 mm about the optical axis of the lens optic 904b. The arches may be either resiliently flexible or relatively flexible or relatively rigid. The spring arms 922b of the lens 900b extend laterally across the outer ends of the haptics opposite the open ends or sides of the haptic openings 918b and are flexible endwise of the lens.

The modified accommodating lens 900c of FIG. 53 is similar in many respects to the lens 900b of FIG. 52 and differs from the latter lens as follows. The spring arms 920b of lens 900b are omitted in the lens 900c. The inner end or bridge portions 914c of the lens haptics 906c are quite short in the endwise direction of the lens. In fact, the length of the inner haptic end portions 914c approximates or is just slightly longer than the width of the open sides of the haptic grooves 916c which form the haptic hinge junctions 908c with the lens optic 904c about which the haptics are flexible anteriorly and posteriorly relative to the optic. As a consequence these hinge junctions occupy or constitute almost the entire length of the inner haptic end portions 914c. The haptic end arches 922c may be either resiliently flexible or relatively rigid.

The lenses 900a, 900b, 900c of FIGS. 51–53 are implanted in the capsular bag of a patient's eye and provide vision accommodation in response to contraction and relaxation of the ciliary muscle in essentially the same manner as the lens 900 of FIGS. 47–50. In the case of lenses 900b, 900c, however, fibrosis occurs through the closed openings 918b, 918c in the lens haptics and about the haptic end arches 922b, 922c to fixate the lenses in the patient's eye. The lens 900c may be sized in length between the outer sides of its arches 922c to fit closely in the capsular bag when the ciliary muscle is relaxed, and these arches may be made resiliently flexible to enable the arches to serve as springs which press against the perimeter of the bag to position the lens in the bag in the same manner as the haptic springs of the earlier described plate haptic spring lenses even though the anterior remnant of the bag may be split, torn, or otherwise not an intact remnant.

Less inert materials utilized for intraocular lens components are preferably selected to provide optimum fixation of lens portions in the peripheral portions of capsular bags, and to provide optimum centration of the lens. Less fibrosis is formed about components formed of inert materials than about less inert materials. The less inert materials result in greater fibrosis being produced about the components. Such materials include PMMA, Acrylic, Prolene (a Nylon) and Polyimide.

Fibrosis forms more tightly about those materials which are less inert, for the reason that the body treats such materials as foreign objects. Lens features such as protuberances, arms and loops, are preferably formed of less inert material, and features intended for relative sliding movement in a capsular bag pocket formed by fibrosis, are formed of more inert materials, such as Silicone, Polyhema (Hydroxethyl methacrylate) or HEMA.

Referring now to FIGS. 54–56, as well as to FIGS. 62 and 63, there is illustrated an anteriorly biased accommodating intraocular lens 1000 according to the invention in its posterior distant vision position within the capsular bag 20 of a patient's eye. Lens 1000 is like the lens earlier described except in the following respects. The anterior surfaces 1002 of the thickened extended portions or plate haptics 1004 of lens 1000 are flush with the anterior surface of the lens optic 1006. The posterior haptic surfaces 1008 incline rearwardly away from the anterior haptic surfaces 1002 from the outer haptic tips toward their inner junctions with the optic 1006 and then forwardly toward the anterior haptic surfaces to define, with the peripheral edge of the optic, posterior V-shaped notches which form thinned flexible hinges 1010 at the inner haptic ends. The optic 1006 has a convexly rounded posterior surface 1012.

Lens 1000 is implanted in the capsular bag 20 in the same manner as the earlier described lenses and is subjected to the same ciliary muscle contraction and relaxation as the earlier described lenses during normal vision accommodation following completion of fibrosis. Lens 1000 is so sized and shaped that the posterior surfaces 1008 of its haptics 1004 and the posterior surface 1012 of its optic 1006 contact the posterior capsule 24 of the bag 20. When the lens 1000 occupies its posterior distant vision configuration of FIGS. 54–56 which it assumes in its posterior distant vision position shown in the latter figures, its hinges 1010 are located a small distance forwardly of the haptic tip plane P of the lens, i.e., a plane passing through the outer tips of the haptics 1004 and the annular haptic-tip-receiving sulcus of the capsular bag 20 normal to the axis of the lens and the eye. Accordingly, during ciliary muscle contraction in the course of normal accommodation, end to end or radial compression of the lens 1000 and vitreous pressure both exert anterior accommodation forces on the lens optic 1006 throughout its full accommodation range. This combined action of the two forces increases the accommodation amplitude and hence diopters of accommodation of the lens.

FIGS. 62 and 63 illustrate two modified anterior biased accommodating intraocular lenses 1000a and 1000b according to the invention implanted within a capsular bag 20 of a patient's eye. These modified anterior biased lenses are identical to and undergo accommodation in much the same manner as the anterior biased lens of FIGS. 54–56 with the following exceptions. In lens 1000a, only the posterior surfaces 1004a of the extended portions or plate haptics 1002a of the lens contact the posterior capsule 24 of the capsular bag. Accordingly, vitreous pressure acts only on these haptics during accommodation, and the lens optic is immune to laser damage during laser capsulotomy of the posterior capsule. The posterior surface 1012a of the lens optic 1006a is spaced from the posterior capsule. In lens 1000b, only the posterior surface 1012b of the lens optic 1006b contacts the posterior capsule 24 of the capsular bag. The posterior surfaces 1004b of the plate haptics 1002b of the lens are spaced from the posterior capsule. Accordingly, during accommodation, vitreous pressure acts only on the posterior surface of the optic.

Most of the accommodating intraocular lenses of the embodiments heretofore described have hinged extended portions in the form of haptics with resiliently flexible haptic hinges. FIGS. 60–61 illustrate modified lenses having extended portions in the form of pivotally hinged haptics. Lens 1100a of FIG. 60 includes a central optic 1102a and plate haptics 1104a (only one shown) extending oppositely from the optic and joined by pivotal hinges 1106a to the edge of the optic. Each haptic hinge comprises mating hinge portions 1108a, 1110a on the respective haptic and the optic, which pivotally interengage and connect the haptics to the optic for anterior and posterior movement of the haptics relative to the optic.

The accommodating intraocular lenses 1100a and 1100c of FIGS. 60 and 61 are made from material not sufficiently firm or hard for the forming of hinge portions, and their hinge portions are separately fabricated of materials suitably hard or firm for reinforcing hinge inserts or inlays, which are molded within the optics and the haptic plates of the lenses. The parts of lenses 1100a and 1100b are designated by the same reference numerals as the corresponding parts, with subscripts a and b for the respective lenses.

The optic and each haptic plate may be molded or otherwise fabricated from any suitable intraocular lens material including materials earlier mentioned. These materials have suitable optical and other qualities for an intraocular lens. Some of the materials are sufficiently hard or firm to enable haptic hinge components to be molded or otherwise formed integrally with the haptic plates, and each haptic hinge groove to be molded or otherwise formed in the material of the lens optic, as shown. Each hinge portion of such embodiment would have a hinge groove or channel along the edge of the optic which opens laterally outward toward the optic, with each hinge groove being cylindrically curved, undercut and sized in transverse cross-section to pivotally receive the bead of the adjacent haptic tongue, whereby the bead is captivated in the groove and the respective haptic is pivotally movable within certain angles anteriorly and posteriorly relative to the optic.

The lens 1100a of FIG. 60 comprises an elongated hinge plate 1120a which is encapsulated and extends edgewise through, forming a reinforcing insert or inlay within, a respective haptic plate 1114a. At the inner end of this hinge plate is a cross-bar 1122a which extends edgewise beyond the inner end of haptic plate 1114a to form the tongue 1112a on the hinge portion 1108a. At the outer end of each hinge plate 1120a are flexible fingers 1124a. Each haptic hinge portion 1110a comprises a bar which is encapsulated within and forms a reinforcing insert or inlay in the edge of the lens optic 1102a. Along the outer edge of the bar is the hinge groove or channel 1118a which pivotally receives the cylindrical bead 1116a along the adjacent hinge tongue 1112a.

The modified lens 1100b of FIG. 61 is like lens 1100a except that the inner end of each haptic plate 1114b extends edgewise beyond the inner cross-bar 1122b of the reinforcing hinge plate which forms the respective haptic hinge portion 1108b of lens 1100b. This extending inner end of each haptic plate 1114b has a cylindrically rounded surface and a central slot 1126b. Each haptic hinge portion comprises a hinge bar 1128b encapsulated in the edge of the lens optic 1102b and having a central rounded hinge projection 1130b. This hinge projection fits rotatably within slot 1126b of hinge portion 1108b, thus to form the respective haptic hinge 1106b with hinge pin 1132b, which extends through aligned bores in the haptic hinge portion in the optic hinge projection.

FIGS. 57–59 illustrate a presently preferred accommodating intraocular lens 1050 according to the invention implanted within a capsular bag 20 of a patient's eye. This preferred lens is an anteriorly biased lens with flexibly hinged extended haptic portions, which achieves increased accommodation amplitude and increased diopters of accommodation by the combined action of (a) its anteriorly biased configuration which increases accommodation amplitude and increased diopters of accommodation, and (b) increased power of its optic which increases the amount of accommodation produced by any given amount of accommodation movement of the lens optic or, conversely, reduces the accommodation movement of the optic required to produce any given amount of accommodation.

Lens 1050 comprises a one piece lens structure having a central optic 1052 and flexibly hinged extended portions 1054 in the form of plate haptics extending generally radially from the optic. Each plate haptic 1054 is longitudinally tapered in width and thickness so as to widen in width and increase in thickness toward its inner end. Each plate haptic includes an inner plate portion 1056 which is integrally joined to an edge of the optic 1052 and inclines anteriorly relative to the optic toward its outer end, an outer plate portion 1058 joined to the outer end of the inner plate portion, and a V-groove 1060 entering at the juncture of these plate portions so as to form at this juncture a flexible hinge 1062. The outer plate portion 1058 is pivotally movable at this hinge anteriorly and posteriorly relative to the inner plate portion 1056 and the optic 1052. The lens structure including its optic and haptic plate portions 1056, 1058 is molded or otherwise formed as a unitary lens structure from a lens material mentioned earlier and has inserts 1064 fixed in the outer ends of the outer haptic plate portions 1058. These inserts provide the lens extended portions or haptics 1054 and may be utilized to reinforce the outer haptic plate portions 1058 if necessary.

Lens 1050 implanted in the capsular bag 20 of the eye with the ciliary muscle of the eye paralyzed in its relaxed state and maintained in this paralyzed state until the completion of fibrosis, all in the same manner as explained earlier. During this fibrosis, the lens optic 1052 is urged posteriorly to its distant vision position shown in solid lines in FIG. 57 and dashed lines in FIG. 58 wherein the posterior surface of the optic presses rearwardly against the posterior capsule 24 of the capsular bag and stretches this posterior capsule rearwardly. The configuration which the lens 1050 assumes or occupies in this posterior distant vision position is its posterior distant vision configuration. Ciliary muscle contraction during normal vision accommodation following completion of fibrosis increases vitreous pressure and compresses the lenses radially or endwise to effect anterior accommodation movement of the lens optic 1052 in the same manner as explained earlier.

As mentioned above, lens 1050 is an anteriorly biased lens. In this regard, it will be observed in FIGS. 57 and 58 that when the lens occupies its posterior distant vision position, its haptic hinges 1062 are located forwardly of a tip plane $P_T$ passing through the outer tips of the lens haptics 1054 normal to the axis of the lens optic 1052 and the eye. Accordingly, compression of the lens by ciliary muscle contraction during normal vision accommodation is effective to produce an anterior accommodation force on the optic throughout its entire accommodation range from its posterior distant vision through its mid-range position (solid lines in FIG. 58) to its anterior near vision position (phantom lines in FIG. 58). Compression of the lens by ciliary muscle contraction thereby aids the anterior vitreous pressure force on the optic throughout its entire accommodation range and thereby increases the accommodation amplitude and diopters of accommodation of the lenses, as explained earlier.

An important feature of lens 1050 is that its optic 1052 has increased optical or dioptic power which aids the anterior biased configuration of the lens to further increase accommodation amplitude and diopters of accommodation. To this end, the anterior face 1066 of the optic is relatively flat or just slightly convex while the posterior face 1068 of the optic has a relatively steep convex curvature such that the optic has a generally planoconvex shape. This optic shape locates most or all of the optical power of the optic at the posterior side of the optic. Increasing the power of the lens optic in this way decreases the distance through which the optic must move to produce any given amount of vision accommodation and, conversely, increases the amount of vision accommodation produced by any given accommodation movement of the optic and thereby increases the maximum accommodation amplitude and diopters of accommodation of the lens.

Increasing the power of an intraocular lens optic at the posterior side of the optic, as in FIGS. 57–58, shifts the optical plane of the optic (i.e. plane from which the focal point of the optic originates) rearwardly toward the retina 16 of the eye. For example, the optical plane $P_O$ of lens optic 1052 is located at the approximate position shown in FIG. 58 which is rearwardly of the optical plane position (not shown) of a symmetrical biconvex optic of the same center thickness measured along the axis of the optic but having anterior and posterior surfaces of equal curvature. This rearward shift of the optical plane of the optic toward the retina must be compensated for by increasing the dioptic power of the optic in order to sharply focus incoming light rays on the retina. The required increase in the power of optic 1052 is accomplished by appropriately shaping the steep convex curvature of the posterior surface 1068 of the optic.

FIG. 64 illustrates an embodiment of the invention which comprises a central optic 1202 and extended portions or haptics 1204 which extend from opposite edge portions of the optic. The optic, in side view, (not shown) is preferably of the configuration shown in FIGS. 58 and 59 to provide the operation and advantages earlier described relative to the embodiment of those figures.

The haptics or extended portions include plates 1206 which have inner ends joined to the optic and with outer free ends, and laterally extending flexible fixation fingers 1208 at the outer ends. Openings 1209 are defined in the outer ends of each fixation finger for improved fixation by fibrosis.

Haptic plates 1206 are longitudinally tapered to narrow in width in the outward direction, and have a width throughout their length less than the diameter of the optic. The haptics and their outer ends are movable anteriorly and posteriorly relative to the optic. Hinges 1210 are defined by grooves in the haptics which enter either anterior or posterior sides and extend across inner end portions of the haptic plates 1206.

The lens has a relatively flat unstressed configuration wherein haptics 1204 and their hinges are disposed in a generally common plane. The outer edges of the haptic plates and the fingers 1208 may preferably be generally circularly curved about the axis of optic 1202. In their normal unstressed state, the fingers extend laterally outwardly from opposite longitudinal edges of respective haptic plates. When unstressed, fingers 1208 are preferably bowed with slight inward curvature.

Deformation of the lens from the normal unstressed configuration by anterior or posterior deflection of the haptics produces elastic strain energy forces in the hinges which urge the lens to its normal unstressed configuration.

FIG. 65A shows a modification of the embodiment of FIG. 65 wherein a recessed pocket 1214 is defined in a haptic portion for accommodating a drug, such as Atropine or a related drug, for paralyzing the ciliary muscles over a time period, or another drug for some other purpose. Such pocket may be provided in both haptics, although FIG. 65 shows only a partial view with only one haptic.

The embodiments of FIGS. 64 and 65 have the flexible fingers 1208 and 1206 on inserts formed of a material different from that of the haptic plates, and preferably of a material which is not particularly inert, thus to effect better fibrosis formation about the fingers and the protuberances 1209. Inert and relatively less inert materials are herein earlier discussed. The haptic plates 1206 are preferably constructed of resilient semi-rigid material.

FIGS. 66 and 67 illustrate somewhat related embodiments of the invention.

The intraocular lens 1300 of FIG. 66 has an optic 1302, preferably configurated, in side view, as shown in FIGS. 58 and 59 to provide the earlier described advantages and operation of the FIG. 59 embodiment of the invention. A plurality of relatively small extension portions or haptic plates 1304 having hinges 1306 to facilitate posterior and anterior movement of the optic in response to ciliary muscle action. The hinges 1306 are defined by grooves in the haptic plates and/or by grooves 1306a in the loops. Hinging action of the plates can alternatively be provided by forming the haptics of a flexible material.

Two pairs of the haptics extend oppositely from the optic, and a loop 1310 extends between each pair of haptics, and is secured to the haptics. An arm 1312 extends from an arcuate transverse portion of each loop 1310 at an acute angle from the transverse portion. Each arm 1312 has an end protuberance defining an opening 1314 for improved fixation and centration.

FIG. 67 illustrates a related embodiment 1350 having an optic 1352, and loops 1354 extending outwardly between pairs of spaced, radially extending small haptics or extension portions 1356. As with the embodiment of FIG. 66, hinging action may be provided by grooves 1357 in the haptics or by grooves 1357a in the loops. An arm 1358 extends from each loop at an acute angle thereto, and has a protuberance 1360 defining a sizable opening at its end, as shown. Improved fibrosis securement and centration, are provided, with or without the opening therein, by the protuberance. The protuberances 1314 of FIG. 66 and 1360 of FIG. 67, preferably with the openings therein, are important features in that they provide substantially improved retention and centration by fibrosis. The arms 1358 and their protuberances 1360, as well as the loops 1354, are preferably formed of a relatively non-inert material for improved fibrosis thereabout.

Thus there has been shown and described a novel accommodating intraocular lens which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

The inventor claims:

1. An accommodating intraocular lens to be implanted in a human eye within a natural capsular bag in the posterior chamber of the eye attached about its perimeter to the ciliary muscle of the eye and having a certain inner diameter when the ciliary muscle is in its relaxed state, the bag including an elastic posterior capsule which is urged anteriorly by vitreous pressure in the eye and an anterior capsule opening bounded by an anterior capsular remnant that fuses to the posterior capsule by fibrosis during a postoperative fibrosis period in which said bag and remnant shrink, and said remnant being tautly stretched by relaxation of the ciliary muscle and relaxed by contraction of the ciliary muscle after fibrosis is complete, said intraocular lens comprising:

a lens body having normally anterior and posterior sides and including an optic and haptics having inner ends joined to diametrically opposite sides of said optic and opposite outer ends, and said haptics being movable anteriorly and posteriorly relative to said optic and through a certain position wherein said lens has a length approximating said inner diameter of said capsular bag, and wherein said lens is adapted to be implanted in said bag while said ciliary muscle is in its relaxed state and in an implanted position wherein (a) said haptics are in said certain position relative to said optic and situated between said remnant and said posterior capsule, whereby fibrosis will occur about the haptics, (b) said optic is aligned with said anterior capsule opening, and (c) shrinking of said bag and remnant during fibrosis will exert endwise compression and posterior forces on the lens and haptics, respectively, and said optic is deflected posteriorly relative to the outer ends of said haptics with resultant anterior deflection of said haptics relative to said optic by endwise compression and posterior forces applied to said lens and haptics, respectively, when said haptics are in said certain position relative to the optic, whereby when said lens is implanted in said bag, relaxation of the ciliary muscle after completion of fibrosis effects posterior deflection of the implanted lens against the posterior capsule of the bag by the taut remnant, and contraction of the ciliary muscle effects anterior accommodation of the implanted lens by the posterior capsule, vitreous pressure, and endwise compression of the lens.

2. An accommodating intraocular lens comprising:

a lens body having normally anterior and posterior sides and including an optic, haptics extending from diametrically opposite sides of said optic and having inner ends adjacent said optic and opposite outer ends, and hinge means pivotally joining said inner haptic ends to said optic for pivotal movement of said haptics about said hinge means anteriorly and posteriorly relative to said optic.

3. An accommodating intraocular lens according to claim 2, wherein:

said hinge means comprise flexible hinge portions of said lens body.

4. An accommodating intraocular lens according to claim 3, wherein:

said hinge portions comprise flexible reduced portions of said lens body.

5. An accommodating intraocular lens to be implanted in a human eye within a capsular bag in the eye having a posterior capsule, and an anterior capsular opening bounded by an anterior capsular remnant, said lens comprising:

a lens body having normally anterior and posterior sides and including an optic and haptics having inner ends hingedly joined to diametrically opposite sides of said optic and opposite outer ends, whereby said haptics are movable anteriorly and posteriorly relative to said optic, and fixation means on said haptics for at least one of the following purposes: (a) positioning the lens in the capsular bag, (b) effecting fixation of the outer haptic ends in the bag by fibrosis.

6. An accommodating intraocular lens comprising:

a lens body having normally anterior and posterior sides and including an optic, and haptics having inner ends joined to diametrically opposite sides of the optic and opposite outer ends, and grooves at one of said body sides extending across said inner haptic ends transverse to the length of the lens and forming hinges about which said haptics are flexible anteriorly and posteriorly relative to said optic.

7. An accommodating lens according to claim 6, wherein: said grooves are located at said anterior side of the body.

8. An intraocular lens to be implanted in a posterior chamber of an eye and supported in the capsular bag of the eye of the user in which a capsulorhexis procedure has been performed, said intraocular lens being adapted to be disposed in the posterior chamber of the eye and having a posterior surface configured to engage the posterior wall of the capsular bag when the lens is in place, and said intraocular lens including a central optical region and two opposing plate-like flexible haptic members attached to said optical region and extending radially outward therefrom, said haptic members being configured and dimensioned to engage the remaining fibrosed circular anterior capsular rim and the posterior capsule to form pockets therein, so that after implantation the intraocular lens is displaced posteriorly by the fibrosed rim to force the intraocular lens against the posterior wall of the capsular bag and to stretch the wall in the posterior direction, whereby contraction of the ciliary muscle of the eye during accommodation relaxes the rim and allows the stretched elastic posteriorly displaced posterior wall of the capsular bag to contract and the haptic members to flex and thus move the intraocular lens in the anterior direction.

9. The intraocular lens defined in claim 8, in which the posterior surface of the optical region is convex to be pressed against the posterior wall of the capsule with the intraocular lens implanted in the eye of the user.

10. An accommodating intraocular lens for implanting within the posterior chamber of a human eye having a natural capsular bag attached about its perimeter to the ciliary muscle of the eye and from which the natural lens matrix has been removed, the bag including an elastic posterior capsule urged anteriorly by vitreous pressure and an anterior capsule opening circumferentially surrounded by a capsular remnant fused by fibrose tissue to the posterior capsule, said lens implant comprising:

an intraocular lens having normally anterior and posterior sides and including a central optic, and haptics extending from opposite edges of the optic and having inner ends joined to the optic and opposite outer end and movable anteriorly and posteriorly relative to said optic, and wherein said intraocular lens is adapted to be disposed in said natural capsular bag and to be so positioned that the optic is aligned with the anterior opening in the natural capsular bag, and the outer ends of said haptics are adapted to be disposed between said remnant and said posterior natural capsule and confined within pockets in the fibrose tissue in a manner such that relaxation of the ciliary muscle effects posterior deflection of the lens and constriction of the ciliary muscle effects anterior accommodation of the lens.

11. An intraocular implant according to claim 10, wherein:

said lens haptics are adapted for deflection by the remnant upon relaxation of the ciliary muscle to reduce vitreous pressure and stretch said remnant to a relatively taut condition to effect posterior deflection of said lens by the remnant to a distant vision position wherein said lens is adapted to press against said posterior capsule and stretch the posterior capsule rearwardly to produce a forward elastic bias force on said lens, and contraction of the ciliary muscle relaxes the capsular remnant and increases vitreous pressure to effect anterior accommodation of the lens by said bias force and vitreous pressure.

12. A lens implant according to claim 10, wherein:

said lens includes fixation means at the outer ends of said haptics to be firmly anchored in said fibrose tissue to positively prevent dislocation of the lens in said capsular bag.

13. An accommodating intraocular lens to be surgically implanted within a natural ocular capsular bag including an elastic posterior capsule urged anteriorly by vitreous pressure and an anterior capsule opening bounded by an anterior capsule rim which fuses by fibrosis to the posterior capsule during a post-operative healing period following surgery with the ciliary muscle paralyzed in its relaxed state, said lens comprising:

a lens body having normally anterior and posterior sides, a central optic having an optic axis, and a plurality of extended flexible portions extending generally radially out from the optic, each extended portion having an inner end connected to the optic and an outer end remote from said inner end movable anteriorly and posteriorly relative to said inner end, said lens adapted for insertion through said anterior capsule opening to an implanted position within said bag in which said extended portions are situated between said rim and posterior capsule for fixation of the lens in the bag and posterior deflection of the lens against said posterior capsule by fibrosis of said rim to said posterior capsule during said healing period, and said extended portions adapted for rearward deflection of said optic upon ciliary muscle relaxation to a posterior distant vision position in which the lens has a posterior distant vision configuration and for forward deflection of said optic upon ciliary muscle contraction to a near vision position, resulting in consistent accommodation of the implanted lens with said contraction and relaxation of the ciliary muscle, and wherein the outer ends of said extended portions are located approximately in a common tip plane normal to said optical axis when said lens has said posterior rear vision configuration, and the inner ends of said extended portions are located in certain positions relative to said plane when said lens has said posterior distant vision configuration, and said certain positions are within the range of positions between and including posterior positions in which the inner ends of said extended portions are located rearwardly of said plane and anterior positions in which said inner ends are located forwardly of said plane, said lens includes hinges at the inner ends of said extended portions pivotally joining said extended portions to said optic for anterior and posterior pivotal movement of said extended portions at said hinges relative to said optic, said hinges occupy posterior positions located rearwardly of said plane when the inner ends of said extended portions are located rearwardly of said plane, and said hinges occupy anterior positions forwardly of said plane when the inner ends of said extended portions are located forwardly of said plane, and inwardly directed forces exerted on the outer ends of said extended portions when said hinges are located rearwardly of said plane urge said optic rearwardly, and inwardly directed forces exerted on said extended portions urge said optic forwardly when said hinges are located forwardly of said plane, and said extended portions adapted to deflect said optic rearwardly upon radial compression of said lens by inwardly directed forces exerted on the outer ends of said extended portions when said inner ends of said extended portions are located rearwardly of said plane, and said extended portions adapted to deflect said optic forwardly upon radial compression of said lens by inwardly directed forces exerted on the outer ends of said extended portions when said inner ends of said extended portions are located forwardly of said plane.

14. An accommodating intraocular lens according to claim 13, wherein:
said hinges are located rearwardly of said plane when said lens has said posterior distant vision configuration.

15. An accommodating intraocular lens according to claim 13, wherein:
said hinges are located forwardly of said plane when said lens has said posterior distant vision configuration.

16. An accommodating intraocular lens according to claim 13, wherein:
each extended portion comprises a T-shaped plate haptic including a plate portion having an inner end connected to said optic, an opposite outer end, and longitudinal edges, and flexible fixation fingers at the outer end of said plate portion extending laterally out from the edges of said plate portion.

17. An accommodating intraocular lens comprising:
a lens body disposed in the posterior chamber of an eye and having normally anterior and posterior sides and including a central optic and extended portions spaced about and extending generally radially out from said optic and having inner ends adjacent to said optic and opposite outer ends movable anteriorly and posteriorly relative to said optic,
said optic has anterior and posterior surfaces,
said extended portions have hinges at the inner ends of said extended portions which accommodate pivotal movement of said extended portions anteriorly and posteriorly relative to said optic at said hinges, and wherein
said posterior surface of said optic is convexly curved to a substantially steeper convex curvature than said anterior surface and provides at least most of the optical power of said optic.

18. An accommodating intraocular lens to be surgically implanted in the posterior chamber of a natural human eye within a natural ocular capsular bag including an elastic posterior capsule urged anteriorly by vitreous pressure and an anterior capsule opening bounded by an anterior capsule rim which fuses by fibrosis to the posterior capsule during a postoperative healing period following surgery with the ciliary muscle paralyzed in its relaxed state, said lens comprising:
a lens body having normally anterior and posterior sides, a central optic having a posterior surface, and a plurality of extended portions extending generally radially out from the optic, each extended portion having an inner end adjacent to the optic, and an outer end remote from said inner end movable anteriorly and posteriorly relative to said inner end,
said extended portions have hinges at the inner ends of said extended portions which accommodate anterior and posterior pivotal movement of said extended portions at said hinges,
said lens adapted for insertion through said anterior capsule opening to an implanted position within said bag in which said extended portions are situated between said rim and posterior capsule for fixation of the lens in the bag and posterior deflection of the lens against said posterior capsule by fibrosis of said rim to said posterior capsule during said healing period, and said extended portions adapted for rearward deflection of said optic under ciliary muscle relaxation to a posterior distant vision position in which the lens has a posterior distant vision configuration and for forward deflection of said optic under ciliary muscle contraction to a near vision position, resulting in consistent accommodation of the implanted lens under said contraction and relaxation of the ciliary muscle, and wherein
said posterior surface of said optic is convexly curved to a substantially steeper convex curvature than said anterior surface and provides at least most of the optical power of said optic.

19. An accommodating intraocular lens for insertion through an opening in an anterior capsule of a natural ocular capsular bag for fixation adjacent to a posterior capsule of the capsular bag, said lens comprising:
a central optic portion having an anterior surface and a posterior surface,
a plurality of extended haptic portions extending radially from the central optic portion, each extended portion having an inner end connected to the central optic portion and an outer end remote from the inner end, each extended portion adapted to permit the lens to fit within the opening formed in the anterior capsule and to permit fixation of the intraocular lens, said extended portions adapted to rearwardly deflect the central optic portion against the posterior capsule under ciliary muscle relaxation, to forwardly deflect the central optic portion under ciliary muscle constriction, and to bias the central optic portion against the posterior capsule during a substantial portion of its movement, resulting in consistent accommodation of the implanted lens with said constriction and relaxation of the ciliary muscle, and wherein
each extended portion comprises one of the following: (a) a rotatably hinged extended portion, (b) a flexibly hinged extended portion, (c) a bendable extended portion.

20. An accommodating intraocular lens to be surgically implanted within a natural ocular capsular bag including an elastic posterior capsule urged anteriorly by vitreous pressure and an anterior capsule opening bounded by an anterior capsule rim which fuses by fibrosis to the posterior capsule during a post operative healing period following surgery with the ciliary muscle paralyzed in its relaxed state, said lens comprising:
a lens body having normally anterior and posterior sides and including an optic having an optic axis, and extended portions spaced apart about the optic,
each said extended portion including a haptic member extending generally radially out from said optic and having an inner end joined to an edge portion of the optic and an opposite outer end, and a pair of resiliently flexible fixation fingers at the outer end of each haptic member and having normal unstressed positions in which the fingers extend laterally in opposite directions from the respective haptic member transversely of said optic,
said fingers being resiliently flexible and bendable from their normal unstressed configurations inwardly toward the optic to deflected positions wherein the fingers conform approximately to a common curvature, and an enlarged protuberance at the outer end of at least one of said fixation fingers and defining an opening therein for improved fixation by fibrosis.

21. An accommodating intraocular lens according to claim 20, wherein:

said lens is adapted for insertion through said anterior capsule opening to an implanted position within said bag in which said extended portions are situated between said rim and posterior capsule for fixation of the lens in the bag and posterior deflection of the lens against said posterior capsule by fibrosis of said rim to said posterior capsule during said healing period, and said extended portions adapted for rearward deflection of said optic under ciliary muscle relaxation to a posterior distant vision position in which the lens has a posterior distant vision configuration and for forward deflection of said optic under ciliary muscle contraction to a near vision position, resulting in consistent accommodation of the implanted lens under said contraction and relaxation of the ciliary muscle.

22. An accommodating intraocular lens according to claim 20, wherein the flexible fixation fingers extend laterally edgewise from the outer end of the extended portions.

23. An accommodating intraocular lens according to claim 20, wherein an enlarged protuberance defining an opening is disposed at the outer end of each of said fixation fingers.

24. An accommodating intraocular lens according to claim 20, and further including a recessed pocket defined in at least one of said extended portions to receive a drug dispensed over a period of time.

25. An accommodating intraocular lens according to claim 24, wherein said drug is Atropine.

* * * * *